(12) United States Patent
Hansen et al.

(10) Patent No.: US 11,830,584 B2
(45) Date of Patent: Nov. 28, 2023

(54) AUTOMATED ELECTRONIC MEDICAL RECORD (EMR) ANALYSIS VIA POINT OF CARE COMPUTING SYSTEMS

(71) Applicant: UnitedHealth Group Incorporated, Minnetonka, MN (US)

(72) Inventors: Kimberly Hansen, Maple Grove, MN (US); Sagran Moodley, Boston, MA (US); Jeff Bishop, Southbury, CT (US); George Bier, St. Paul, MN (US); Anupam Goel, Clarendon Hills, IL (US)

(73) Assignee: UnitedHealth Group Incorporated, Minnetonka, MN (US)

( * ) Notice: Subject to any disclaimer, the term of this patent is extended or adjusted under 35 U.S.C. 154(b) by 193 days.

(21) Appl. No.: 16/689,289

(22) Filed: Nov. 20, 2019

(65) Prior Publication Data

US 2020/0160948 A1 May 21, 2020

Related U.S. Application Data

(60) Provisional application No. 62/834,665, filed on Apr. 16, 2019, provisional application No. 62/769,895, filed on Nov. 20, 2018.

(51) Int. Cl.
*G16H 15/00* (2018.01)
*G16H 10/60* (2018.01)
(Continued)

(52) U.S. Cl.
CPC ............. *G16H 15/00* (2018.01); *G06F 21/31* (2013.01); *G06Q 30/0206* (2013.01);
(Continued)

(58) Field of Classification Search
None
See application file for complete search history.

(56) References Cited

U.S. PATENT DOCUMENTS 8,265,954 B2 9/2012 Hasan et al.
8,428,966 B2 4/2013 Green, III et al.
(Continued)

FOREIGN PATENT DOCUMENTS

WO 2016/138102 A1 9/2016
WO 2021/076652 A1 4/2021

OTHER PUBLICATIONS

Fair Health Consumer; www.fairhealthconsumer.org, accessed via web.archive.org for Dec. 23, 2017 (Year: 2017).*
(Continued)

*Primary Examiner* — Evangeline Barr
*Assistant Examiner* — Anne-Marie K Alderson
(74) *Attorney, Agent, or Firm* — Alston & Bird LLP

(57) ABSTRACT

A care estimate module operating on a central computing entity receives a trigger indication (a) comprising patient identifying information and (b) that identifies a service; extracts the patient identifying information from the trigger indication; determines the service; identifies a potential provider that provides the service; and determines a care estimate for the potential provider to provide the service to the patient. The potential provider is identified based on eligibility information associated with the patient, a location associated with the patient, and an address associated with the potential provider. The care estimate is determined based on the eligibility information associated with the patient. The central computing entity generates a care estimate notification that identifies the potential provider and com-
(Continued)

prises the care estimate; and provides the care estimate notification such that a user computing entity receives the care estimate notification.

16 Claims, 15 Drawing Sheets

(51) Int. Cl.
*G16H 40/00* (2018.01)
*G16H 80/00* (2018.01)
*G06Q 40/08* (2012.01)
*G06F 21/31* (2013.01)
*G06Q 30/0201* (2023.01)

(52) U.S. Cl.
CPC .............. *G06Q 40/08* (2013.01); *G16H 10/60* (2018.01); *G16H 40/00* (2018.01); *G16H 80/00* (2018.01)

(56) References Cited

U.S. PATENT DOCUMENTS

| | | | |
|---|---|---|---|
| 8,909,593 | B2 | 12/2014 | Patel et al. |
| 9,710,600 | B1 | 7/2017 | Dunleavy et al. |
| 10,170,203 | B1 | 1/2019 | Blechman |
| 10,276,263 | B2 | 4/2019 | Connely et al. |
| 10,296,715 | B1 | 5/2019 | Smith et al. |
| 10,586,615 | B2 | 3/2020 | Bastide et al. |
| 10,742,654 | B1 | 8/2020 | Pinsonneault et al. |
| 10,799,189 | B2 | 10/2020 | Nye et al. |
| 10,990,352 | B1 | 4/2021 | Artz et al. |
| 11,031,109 | B2 | 6/2021 | Devarakonda et al. |
| 11,101,026 | B2 | 8/2021 | Francois et al. |
| 11,120,906 | B2 | 9/2021 | Gandy et al. |
| 11,392,669 | B1 | 7/2022 | Jaladi et al. |
| 2003/0191669 | A1 | 10/2003 | Fitzgerald et al. |
| 2004/0111296 | A1 | 6/2004 | Rosenfeld et al. |
| 2007/0162308 | A1 | 7/2007 | Peters |
| 2009/0254368 | A1 | 10/2009 | Cunnold |
| 2009/0271218 | A1 | 10/2009 | Mok et al. |
| 2011/0106564 | A1* | 5/2011 | Hachmeister .......... G16H 30/20 705/3 |
| 2012/0129139 | A1 | 5/2012 | Partovi |
| 2012/0166226 | A1* | 6/2012 | Lee ........................ G06Q 10/10 705/3 |
| 2012/0271612 | A1 | 10/2012 | Barsoum et al. |
| 2013/0054264 | A1 | 2/2013 | Baronov et al. |
| 2013/0085779 | A1 | 4/2013 | Vilsmeier |
| 2013/0096938 | A1 | 4/2013 | Stueckemann et al. |
| 2013/0110755 | A1 | 5/2013 | Upadhyayula et al. |
| 2013/0179189 | A1 | 7/2013 | Brown |
| 2013/0191135 | A1* | 7/2013 | Camacho ............... G16H 10/60 705/2 |
| 2013/0191157 | A1 | 7/2013 | Eiden et al. |
| 2013/0332194 | A1 | 12/2013 | D'Auria et al. |
| 2014/0039911 | A1* | 2/2014 | Iyer .................... G06Q 30/0207 705/2 |
| 2014/0058742 | A1 | 2/2014 | Chari et al. |
| 2014/0136233 | A1 | 5/2014 | Atkinson et al. |
| 2014/0236630 | A1 | 8/2014 | Murata |
| 2014/0278534 | A1 | 9/2014 | Romeo |
| 2014/0372141 | A1 | 12/2014 | Renner et al. |
| 2015/0019248 | A1 | 1/2015 | Anand et al. |
| 2015/0039343 | A1* | 2/2015 | Cline ..................... G16H 10/60 705/3 |
| 2015/0046173 | A1 | 2/2015 | Furletti et al. |
| 2015/0066539 | A1 | 3/2015 | Sheffer et al. |
| 2015/0081332 | A1 | 3/2015 | Casper et al. |
| 2015/0213195 | A1 | 7/2015 | Blechman |
| 2015/0242955 | A1 | 8/2015 | Long et al. |
| 2015/0294089 | A1 | 10/2015 | Nichols |
| 2016/0012187 | A1 | 1/2016 | Zasowski et al. |
| 2016/0055314 | A1 | 2/2016 | Anderson et al. |
| 2016/0125550 | A1 | 5/2016 | Joao et al. |
| 2016/0180030 | A1 | 6/2016 | Gunawardena et al. |
| 2016/0253687 | A1 | 9/2016 | Wei et al. |
| 2016/0285876 | A1 | 9/2016 | Perez et al. |
| 2016/0357910 | A1 | 12/2016 | Ghouri et al. |
| 2016/0357915 | A1 | 12/2016 | Morris et al. |
| 2016/0357932 | A1 | 12/2016 | Morris et al. |
| 2016/0358288 | A1 | 12/2016 | McKenzie et al. |
| 2017/0109478 | A1 | 4/2017 | Hasan et al. |
| 2017/0161435 | A1* | 6/2017 | Orosco .................. G16H 10/60 |
| 2017/0161439 | A1* | 6/2017 | Raduchel ................ G06F 21/31 |
| 2017/0262604 | A1 | 9/2017 | Francois |
| 2017/0300647 | A1 | 10/2017 | Goldberg et al. |
| 2017/0372430 | A1 | 12/2017 | Maddison et al. |
| 2018/0046764 | A1 | 2/2018 | Katwala et al. |
| 2018/0102190 | A1 | 4/2018 | Hogue et al. |
| 2018/0121843 | A1 | 5/2018 | Connely, IV et al. |
| 2018/0181720 | A1 | 6/2018 | Ensey et al. |
| 2018/0286509 | A1 | 10/2018 | Shah et al. |
| 2019/0096534 | A1 | 3/2019 | Joao |
| 2019/0208354 | A1 | 7/2019 | Raduchel et al. |
| 2019/0244683 | A1 | 8/2019 | Francois |
| 2019/0279753 | A1 | 9/2019 | Rourke et al. |
| 2020/0160955 | A1 | 5/2020 | Hansen et al. |
| 2020/0167879 | A1 | 5/2020 | Patel et al. |
| 2020/0176089 | A1 | 6/2020 | Jones et al. |
| 2020/0342969 | A1 | 10/2020 | White et al. |
| 2020/0410601 | A1 | 12/2020 | Laumeyer et al. |
| 2021/0012904 | A1 | 1/2021 | Simon et al. |
| 2021/0045682 | A1 | 2/2021 | Poon et al. |
| 2021/0142914 | A1 | 5/2021 | Hua et al. |
| 2021/0151180 | A1 | 5/2021 | Sudharsan |

OTHER PUBLICATIONS

International Searching Authority, Invitation to Pay Additional Fees and Partial Search Report for International Application No. PCT/US2019/062459, dated Feb. 19, 2020, (18 pages), European Patent Office, Rijswijk, The Netherlands.
"Centricity Payer Connect," YouTube Video, GE Healthcare, (35 pages), Jun. 14, 2018. [Retrieved from the Internet Feb. 12, 2020]<https://www.youtube.com/watch?v=YD9RiCRjVu8&feature=youtu.be>.
"Payer-Provider Integration," YouTube Video, emids, Sep. 2, 2015, (7 pages). [Retrieved from the Internet Feb. 12, 2020] <https://www.youtube.com/watch?v=z_ByQh8-tUY>.
International Searching Authority, International Search Report and Written Opinion, dated Jun. 24, 2020, (19 pages), European Patent Office, Rijswijk, Netherlands.
NonFinal Office Action for U.S. Appl. No. 16/689,288, dated Jul. 23, 2021, (33 pages), United States Patent and Trademark Office, USA.
NonFinal Office Action for U.S. Appl. No. 16/689,314, dated May 10, 2021, (48 pages), United States Patent and Trademark Office, USA.
"Point of Care Assist, Powered by RxRevu," Cerner, (6 pages), (article, online), [Retrieved from the Internet Sep. 22, 2021] <URL: https://code.cerner.com/apps/rxrevu>.
"Premera—Prior Authorization," (25 pages), (article, online), https://www.premera.com/documents/036791.pdf.
Final Office Action for U.S. Appl. No. 16/689,288, dated Sep. 8, 2021, (18 pages), United States Patent and Trademark Office, USA.
Saiyed, Salim M. et al. "Differences, Opportunities, and Strategies in Drug Alert Optimization—Experiences of Two Different Integrated Health Care Systems," Applied Clinical Informatics, vol. 10, No. 5, pp. 777-782, DOI: 10.1055/s-0039-1697596.
Zahabi, Maryam et al. "Usability and Safety in Electronic Medical Records Interface Design: A Review of Recent Literature and Guideline Formulation," Human Factors The Journal of the Human Factors and Ergonomics, vol. 57, Issue 5, pp. 805-834, Published online: Mar. 23, 2015, Issue published: Aug. 1, 2015, DOI: 10.1177/0018720815576827.
Final Office Action for U.S. Appl. No. 16/689,314, dated Nov. 22, 2021, (73 pages), United States Patent and Trademark Office, USA.
Advisory Action for U.S. Appl. No. 16/689,288, dated Oct. 20,

(56) References Cited

OTHER PUBLICATIONS 2021, (4 pages), United States Patent and Trademark Office, USA.
Gu, Yingqi et al. "Predicting Medication Adherence Using Ensemble Learning and Deep Learning Models With Large Scale Healthcare Data," Scientific Reports, vol. 11, No. 18961, Sep. 23, 2021, pp. 1-13, available online: https://www.nature.com/articles/s41598-021-98387-w.
NonFinal Office Action for U.S. Appl. No. 16/689,288, dated Feb. 18, 2022, (25 pages), United States Patent and Trademark Office, USA.
NonFinal Office Action for U.S. Appl. No. 16/689,314, dated May 16, 2022, (68 pages), United States Patent and Trademark Office, US.
Final Office Action for U.S. Appl. No. 16/689,314, dated Nov. 23, 2022, (67 pages), United States Patent and Trademark Office, US.
Final Office Action for U.S. Appl. No. 16/689,288, dated Sep. 6, 2022, (21 pages), United States Patent and Trademark Office, US.
NonFinal Office Action for U.S. Appl. No. 16/689,288, dated Mar. 3, 2023, (16 pages), United States Patent and Trademark Office, US.
NonFinal Office Action for U.S. Appl. No. 16/689,314, dated Jul. 27, 2023, (36 pages), United States Patent and Trademark Office, US.
Final Rejection dated Sep. 6, 2023 for U.S. Appl. No. 16/689,288, 17 page(s).

* cited by examiner

PATIENT CHART: AMANDA JONES — 1002

Patient Information

Name: Amanda Jones
Preferred Name: Mandy
Sex: Female
Date of Birth: 03/02/1953
Age: 66
Social Security Number: XXX-XX-4599
Patient Number: 12343456
Health Plan: Insurance-Is-Us Premium
Member ID: 90897867

Contact Information — 1004

Address: 111 Street Lane
Chaska, MN 55318
Email address: ajones@email.com
Phone Numbers:
  Cell: 952-555-1234
  Home: 952-555-5678
  Office: 952-555-9012

Medications [ADD]

Insulin Glulisine (Apidra) 3 ml 5 solo pen
Lanoxin 125 mcg tablet
Repaglinide (Prandin) 1 mg tablet
Alogiptin (Nesina) 25 mg tablet
Bromocriptine (Parlodel) 2.5 mg TAB — 1006

Care Gap Evaluation

No Gaps in Care Identified — 1008

Medical History — 1010

Conditions: — 1012
Anemia
Type II Diabetic
Depression/Anxiety [ADD]

Tests/Procedures:
Hemoglobin A1C                    10/20/2018
CBC Platelet with Differential    10/20/2018
Hemoglobin A1C                    10/23/2019
Bilateral Screening Mamogram      9/08/2019

[VIEW MORE] — 1014
[CARE ESTIMATE] — 1016

1018 (ADD buttons), 1000, 316

FIG. 10

AUTOMATED ELECTRONIC MEDICAL RECORD (EMR) ANALYSIS VIA POINT OF CARE COMPUTING SYSTEMS

CROSS-REFERENCE TO RELATED APPLICATIONS

This application claims priority to U.S. Application No. 62/769,895, filed Nov. 20, 2018, and U.S. Application No. 62/834,665, filed Apr. 16, 2019, the contents of which are hereby incorporated by reference in their entireties.

TECHNICAL FIELD

Various embodiments relate to user interfaces for providing care gap evaluations and care estimate evaluations. Various embodiments relate to back-end functionality that may be integrated into various front-end electronic medical record (EMR) systems operable at least in part at point of care computing systems.

BACKGROUND

Various electronic medical record (EMR) and/or practice management systems are available for use by various healthcare providers, provider groups, clinics, hospitals, and/or the like, referred to herein as providers. An insurance company and/or payor system may need to communicate with a plurality of provider computing entities corresponding to various providers. Thus, an insurance company and/or payor system may need to communicate with a plurality of different EMR and/or practice management systems and/or provide back-end functionality to a plurality of different EMR and/or practice management systems. However, the variety of different EMR and/or practice management systems can make providing back end functionality difficult.

BRIEF SUMMARY OF SOME EXAMPLE EMBODIMENTS

Various embodiments provide methods, systems, apparatus, computer program products, and/or the like for providing back-end functionality to a variety of front end and/or user-facing EMR and/or practice management systems which may be operable at least in part at point of care computing systems. In various embodiments, the back-end functionality includes generating and providing a care gap evaluation, generating and providing a care estimate evaluation, and/or the like. In various embodiments, the care gap evaluation, care estimate evaluation, and/or the like may be provided via an interactive user interface (IUI) of the EMR and/or practice management system. For example, when an appointment is scheduled via an IUI of the EMR and/or practice management system, as part of the appointment scheduling workflow, the care gap evaluation and/or care estimate evaluation may be provided via the IUI such that the care gap evaluation and/or care estimate evaluation appears as integrated functionality of the IUI of the EMR and/or practice management system. In another example, when, via the IUI of the EMR and/or practice management system, labs and/or other tests are ordered and/or a prescription is entered for a patient/member, a care estimate evaluation may be provided to the user via the provider computing entity and/or a corresponding patient/member computing entity. The care estimate evaluation may be provided via the corresponding patient/member computing entity via a variety of formats, some examples of which include: short message service (SMS) message, multimedia message service (MMS) message, instant message, email, an online portal, a dedicated application, and/or the like.

Additionally, at least some of the information/data being accessed and/or analyzed by the back-end functionality is private information/data (e.g., Health Insurance Portability and Accountability Act (HIPAA) protected information/data and/or the like). Thus, various embodiments provide integrated back-end functionality for various EMR and/or practice management systems that maintains the privacy of sensitive patient/member information/data.

According to one aspect, a method for providing a care gap evaluation via an interactive user interface provided by a user computing entity is provided. In an example embodiment, the method comprises receiving, by a care gap module operating on a central computing entity, a trigger indication comprising patient identifying information that identifies a patient. The method further comprises extracting, by the care gap module, the patient identifying information from the trigger indication; and querying, by the central computing entity, a plurality of care standards stored in a memory media to identify one or more care standards relevant to the patient based on at least one of (a) demographic information corresponding to the patient or (b) medical history information corresponding to the patient. The method further comprises analyzing, by the central computing entity, the medical history information corresponding to the patient based on the one or more care standards to identify whether the medical history information is missing any data items indicative of gaps in care; and generating, by the central computing entity, a care gap notification that indicates whether any gaps in care were identified and, when a gap in care was identified, indicates what the gap was. The method further comprises providing, by the central computing entity, the care gap notification such that a user computing entity receives the care gap notification. The user computing entity may be configured to provide a care gap evaluation comprising at least a portion of the care gap notification or a graphical representation thereof via a user interface of the user computing entity.

According to another aspect, an apparatus is provided. In an example embodiment, the apparatus is a central computing entity. In an example embodiment, the apparatus comprises at least one processor, at least one communications interface, and at least one memory including computer program code. The computer program code comprises executable instructions corresponding to a care gap module. The at least one memory and computer program code are configured to, with the processor, cause the apparatus to at least receive, by the care gap module, a trigger indication comprising patient identifying information that identifies a patient; extract, by the care gap module, the patient identifying information from the trigger indication; query a plurality of care standards stored in a memory media to identify one or more care standards relevant to the patient based on at least one of (a) demographic information corresponding to the patient or (b) medical history information corresponding to the patient; analyze, by the care gap module, the medical history information corresponding to the patient based on the one or more care standards to identify whether the medical history information is missing any data items indicative of gaps in care; generate a care gap notification that indicates whether any gaps in care were identified and, when a gap in care was identified, indicates what the gap was; and provide the care gap notification such that a user computing entity receives the care gap notification. The user computing entity may be configured to provide a care gap evaluation comprising at least a portion of the care gap notification or a graphical representation thereof via a user interface of the user computing entity.

According to yet another aspect, a computer program product is provided. In an example embodiment, the computer program product comprises at least one non-transitory computer-readable storage medium having computer-executable program code portions stored therein. The computer-executable program code portions comprise program code instructions corresponding a care gap module. The computer program code instructions, when executed by a processor of a computing entity, are configured to cause the computing entity to receive, by the care gap module, a trigger indication comprising patient identifying information that identifies a patient; extract, by the care gap module, the patient identifying information from the trigger indication; query a plurality of care standards stored in a memory media to identify one or more care standards relevant to the patient based on at least one of (a) demographic information corresponding to the patient or (b) medical history information corresponding to the patient; analyze, by the care gap module, the medical history information corresponding to the patient based on the one or more care standards to identify whether the medical history information is missing any data items indicative of gaps in care; generate a care gap notification that indicates whether any gaps in care were identified and, when a gap in care was identified, indicates what the gap was; and provide the care gap notification such that a user computing entity receives the care gap notification. The user computing entity may be configured to provide a care gap evaluation comprising at least a portion of the care gap notification or a graphical representation thereof via a user interface of the user computing entity. In an example embodiment, the computing entity is a central computing entity.

According to still another aspect a method for providing a care estimate evaluation via an interactive user interface provided by a user computing entity. In an example embodiment, the method comprises receiving, by a care estimate module operating on a central computing entity, a trigger indication (a) comprising patient identifying information that identifies a patient and (b) that identifies at least one service. The method further comprises extracting, by the care estimate module, the patient identifying information from the trigger indication; determining, by the care estimate module, the at least one service; and identifying, by the care estimate module, at least one potential provider that provides the at least one service. The at least one potential provider is identified based at least in part on eligibility information associated with the patient, a location associated with the patient, and an address associated with the at least one potential provider. The method further comprises determining, by the care estimate module, a cost estimate for the at least one potential provider to provide the at least one service to the patient. The cost estimate is determined at least in part based on the eligibility information associated with the patient. The method further comprises generating, by the central computing entity, a care estimate notification that identifies the at least one potential provider and comprises the cost estimate; and providing, by the central computing entity, the care estimate notification such that a user computing entity receives the care estimate notification. The user computing entity may be configured to provide a care estimate evaluation comprising at least a portion of the care estimate notification or a graphical representation thereof via a user interface of the user computing entity.

According to another aspect, an apparatus is provided. In an example embodiment, the apparatus is a central computing entity. In an example embodiment, the apparatus comprises at least one processor, at least one communications interface, and at least one memory including computer program code. The computer program code comprising executable instructions corresponding to a care estimate module. The at least one memory and computer program code configured to, with the processor, cause the apparatus to at least receive, by the care estimate module, a trigger indication (a) comprising patient identifying information that identifies a patient and (b) that identifies at least one service; extract, by the care estimate module, the patient identifying information from the trigger indication; determine, by the care estimate module, the at least one service; identify, by the care estimate module, at least one potential provider that provides the at least one service, the at least one potential provider identified based at least in part on eligibility information associated with the patient, a location associated with the patient, and an address associated with the at least one potential provider; determine, by the care estimate module, a cost estimate for the at least one potential provider to provide the at least one service to the patient, the cost estimate determined at least in part based on the eligibility information associated with the patient; generate a care estimate notification that identifies the at least one potential provider and comprises the cost estimate; and provide the care estimate notification such that a user computing entity receives the care estimate notification. The user computing entity may be configured to provide a care estimate evaluation comprising at least a portion of the care estimate notification or a graphical representation thereof via a user interface of the user computing entity.

In yet another aspect, a computer program product is provided. In an example embodiment, the computer program product comprises at least one non-transitory computer-readable storage medium having computer-executable program code portions stored therein. The computer-executable program code portions comprise program code instructions corresponding a care estimate module. The computer program code instructions, when executed by a processor of a computing entity, are configured to cause the computing entity to receive, by the care estimate module, a trigger indication (a) comprising patient identifying information that identifies a patient and (b) that identifies at least one service; extract, by the care estimate module, the patient identifying information from the trigger indication; determine, by the care estimate module, the at least one service; identify, by the care estimate module, at least one potential provider that provides the at least one service, the at least one potential provider identified based at least in part on eligibility information associated with the patient, a location associated with the patient, and an address associated with the at least one potential provider; determine, by the care estimate module, a cost estimate for the at least one potential provider to provide the at least one service to the patient, the cost estimate determined at least in part based on the eligibility information associated with the patient; generate a care estimate notification that identifies the at least one potential provider and comprises the cost estimate; and provide the care estimate notification such that a user computing entity receives the care estimate notification. The user computing entity may be configured to provide a care estimate evaluation comprising at least a portion of the care estimate notification or a graphical representation thereof via a user interface of the user computing entity. In an example embodiment, the computing entity is a central computing entity.

According to still another aspect, a method for providing an integrated back-end computing function of a practice management system is provided. In an example embodiment, the method comprises receiving, by a central computing entity, an encrypted request for performance of a back-end function. The encrypted request is associated with a provider and a corresponding practice management system. The method further comprises generating, by the central computing entity, a trigger indication that comprises patient identifying information based on the encrypted request; processing the trigger indication using a program code module corresponding to the back-end function and operating on the central computing entity to generate a response; converting, by the central computing entity, the response into a notification in a format corresponding to the practice management system; and encrypting and providing, by the central computing entity, the notification such that a user computing entity receives the notification. In an example embodiment, the user computing entity is configured to provide at least a part of the notification or a graphical representation thereof via a user interface of the user computing entity.

According to another aspect, an apparatus is provided. In an example embodiment, the apparatus is a central computing entity. In an example embodiment, the apparatus comprises at least one processor, at least one communications interface, and at least one memory including computer program code. The at least one memory and computer program code configured to, with the processor, cause the apparatus to at least receive an encrypted request for performance of a back-end function, the encrypted request associated with a provider and a corresponding practice management system; based on the encrypted request, generate a trigger indication that comprises patient identifying information; process the trigger indication using a program code module corresponding to the back-end function and operating on the apparatus to generate a response; convert the response into a notification in a format corresponding to the practice management system; and encrypt and provide the notification such that a user computing entity receives the notification. The user computing entity may be configured to provide at least a part of the notification or a graphical representation thereof via a user interface of the user computing entity.

According to yet another aspect, a computer program product is provided. In an example embodiment, the computer program product comprises at least one non-transitory computer-readable storage medium having computer-executable program code portions stored therein. The computer program code instructions, when executed by a processor of a computing entity, are configured to cause the computing entity to receive an encrypted request for performance of a back-end function, the encrypted request associated with a provider and a corresponding practice management system; based on the encrypted request, generate a trigger indication that comprises patient identifying information; process the trigger indication using a program code module corresponding to the back-end function and operating on the computing entity to generate a response; convert the response into a notification in a format corresponding to the practice management system; and encrypt and provide the notification such that a user computing entity receives the notification. The user computing entity may be configured to provide at least a part of the notification or a graphical representation thereof via a user interface of the user computing entity. In an example embodiment, the computing entity is a central computing entity.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

Figure 4:
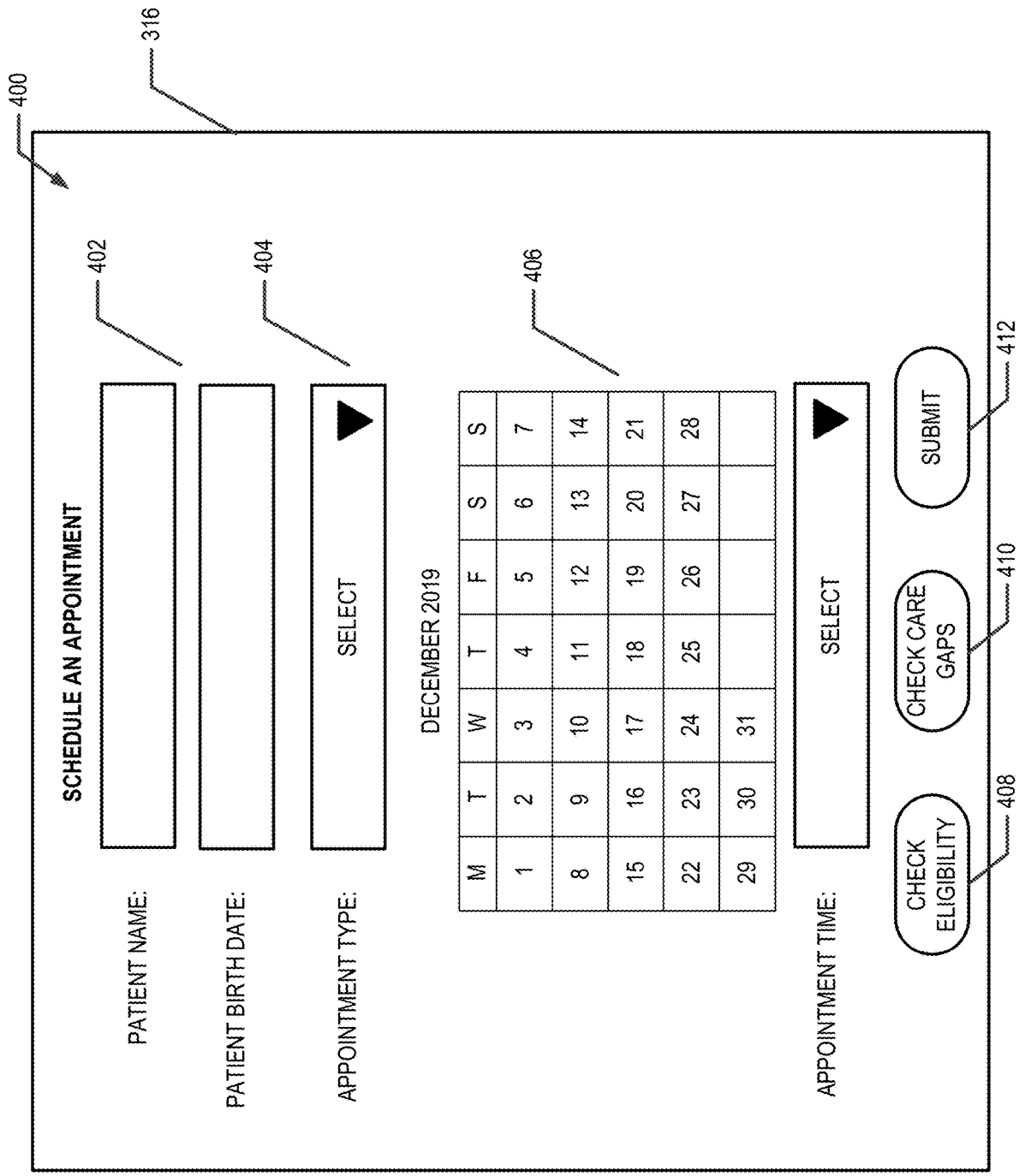
Figure 5:
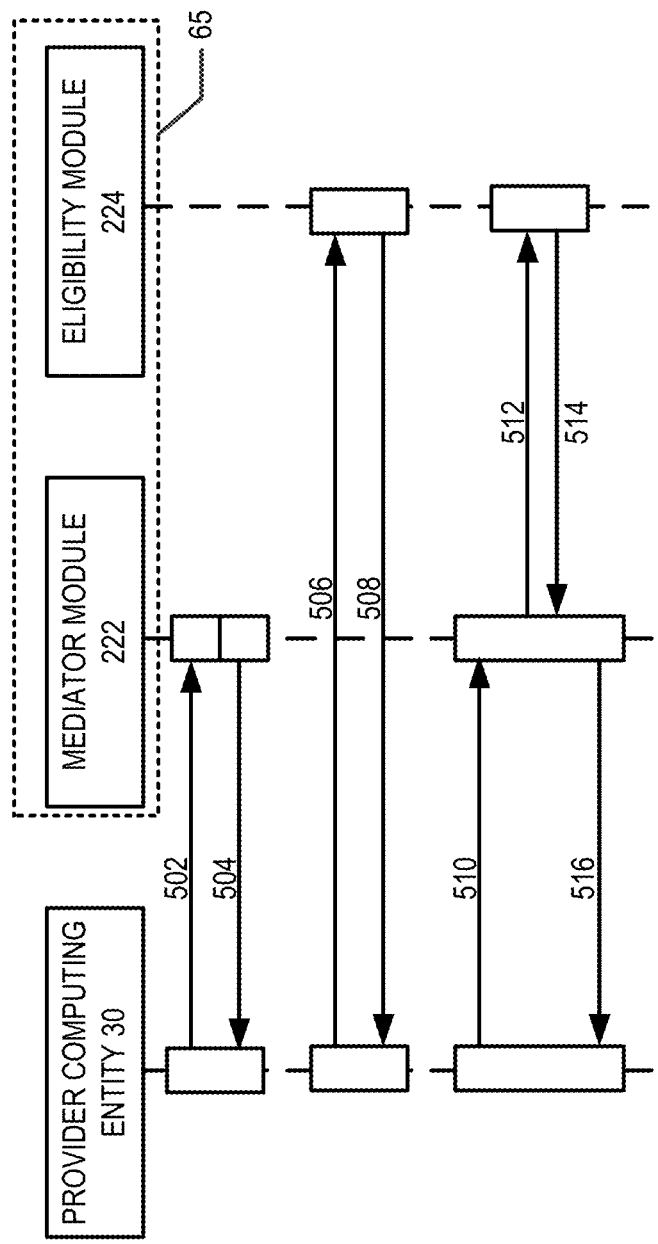
Figure 6:
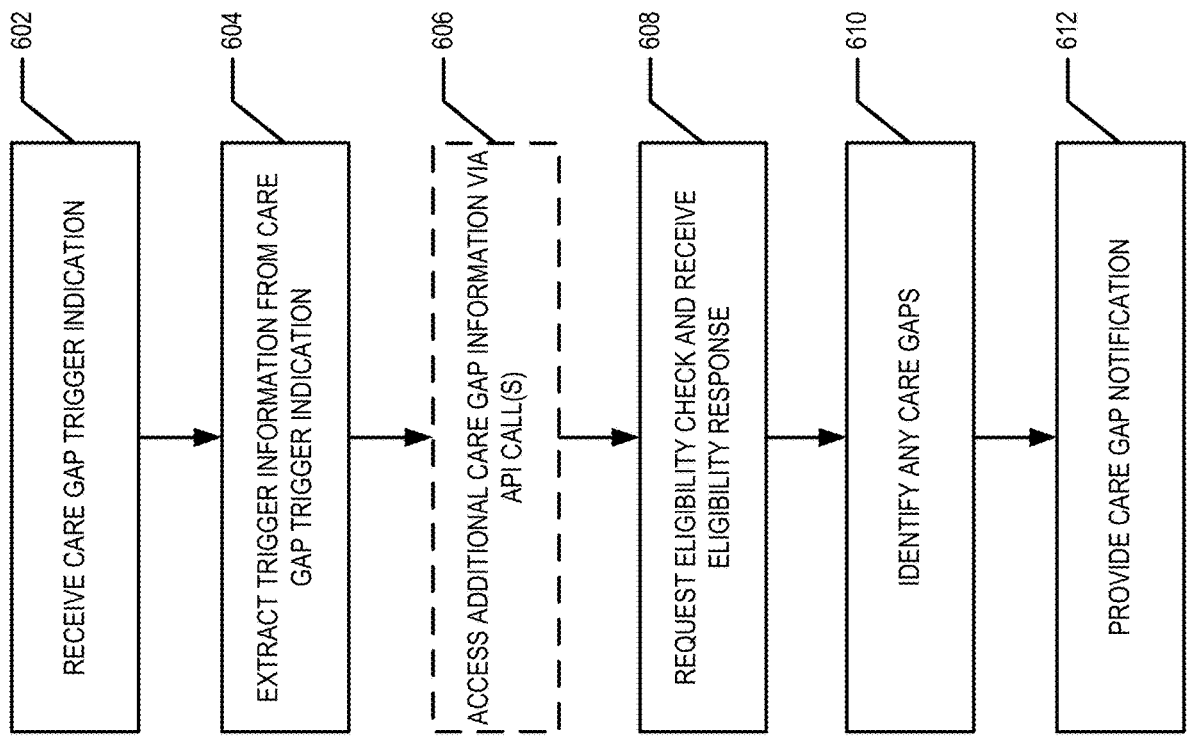
Figure 7:
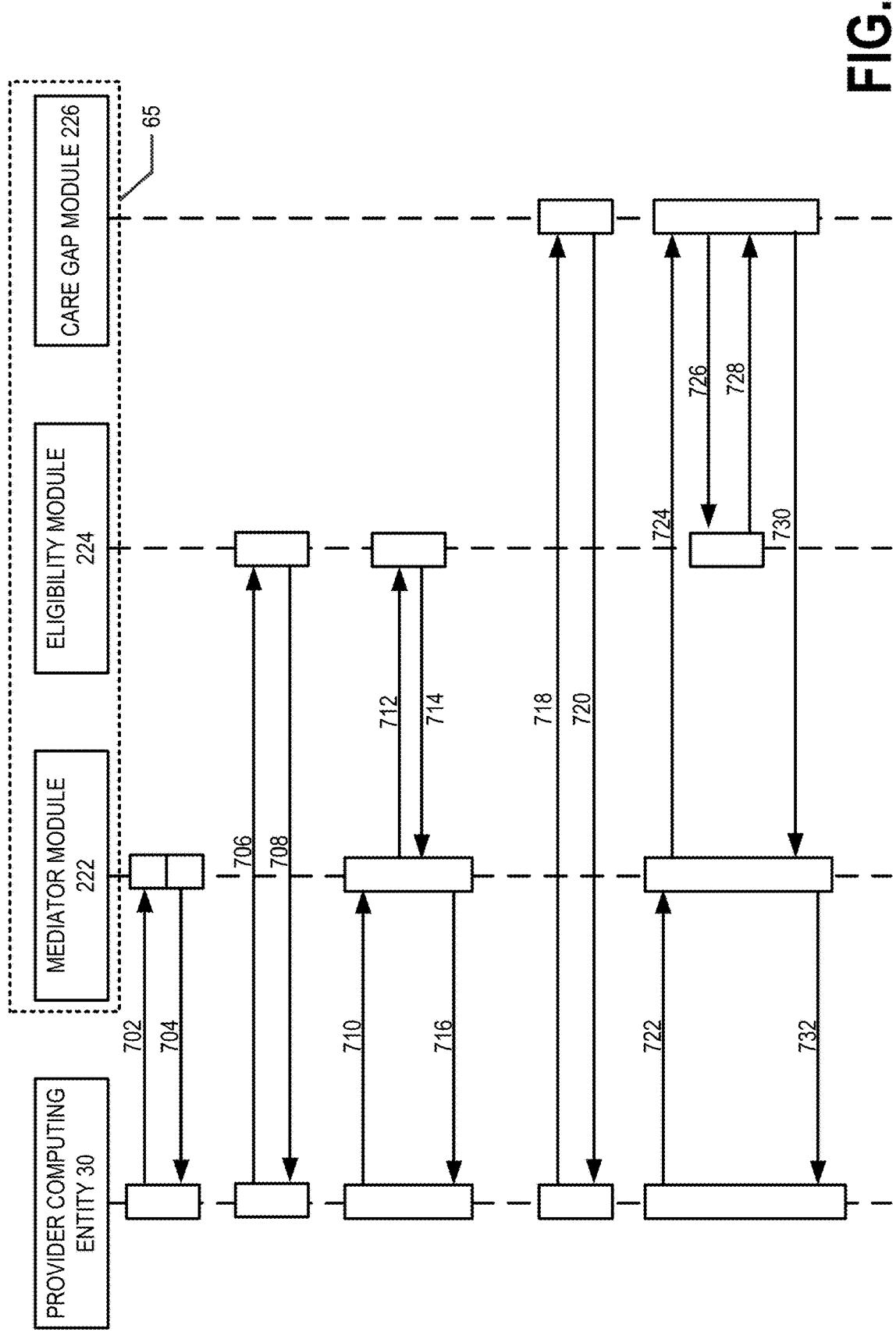
Figure 8:
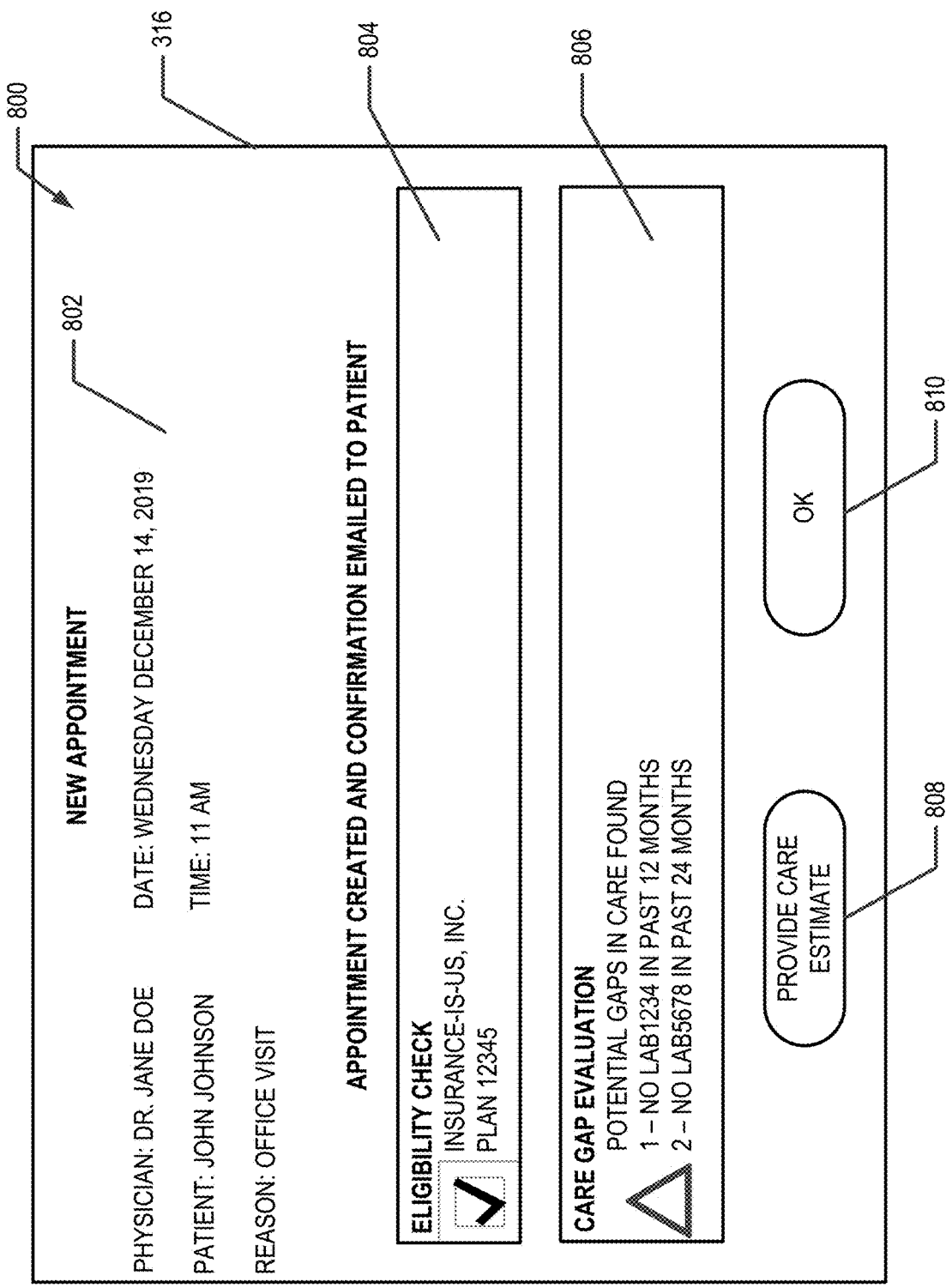
Figure 9:
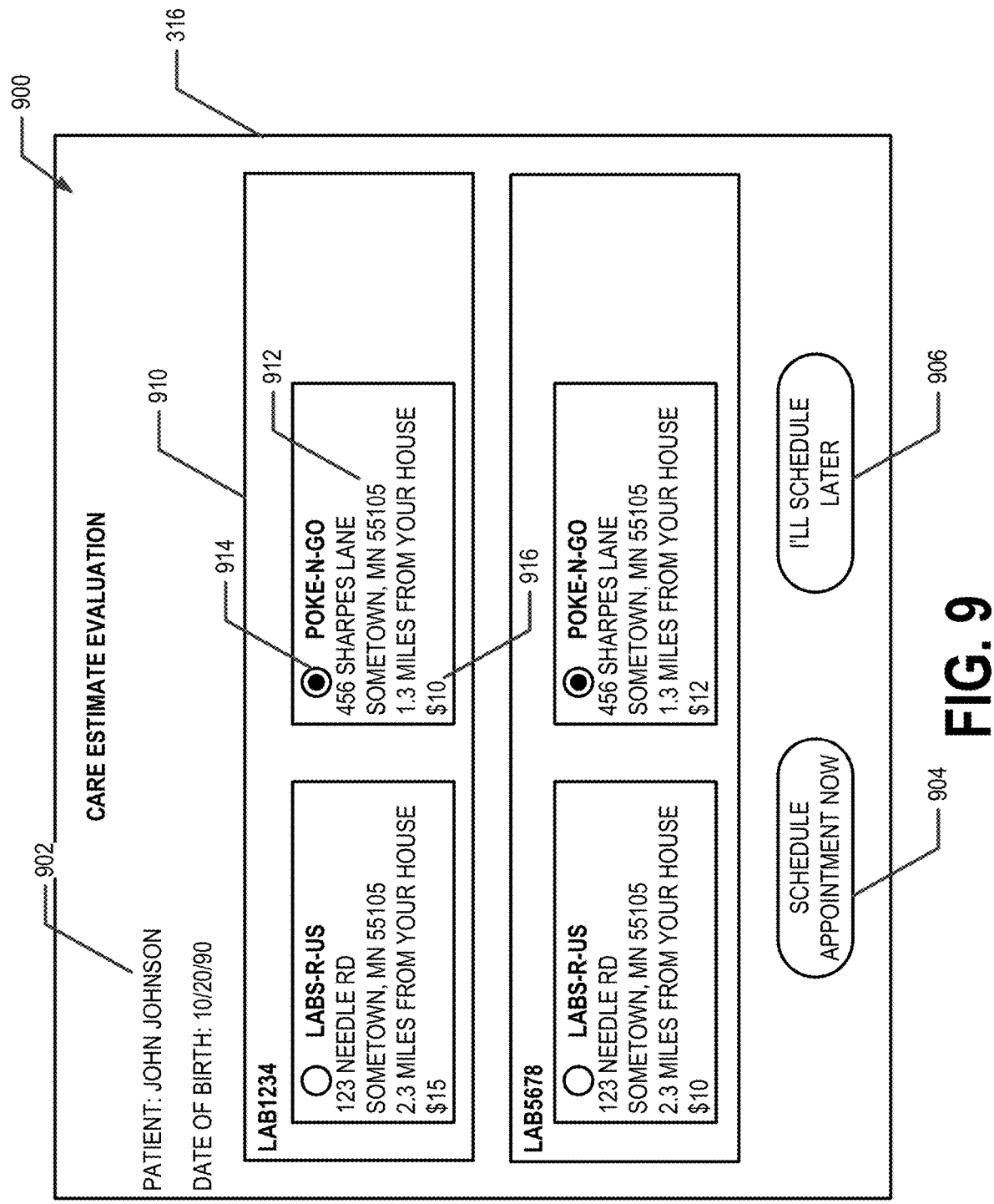
Figure 11:
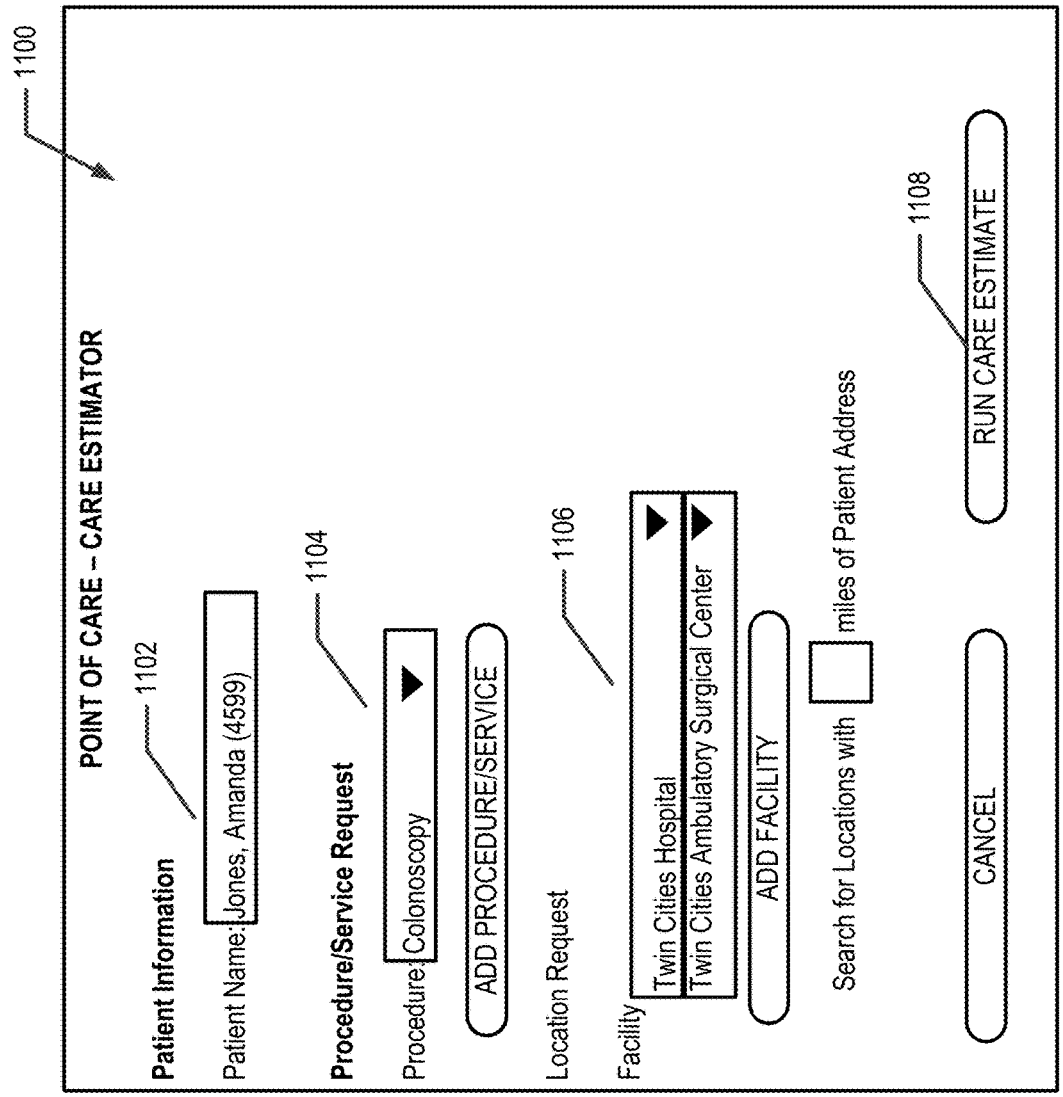
Figure 12:
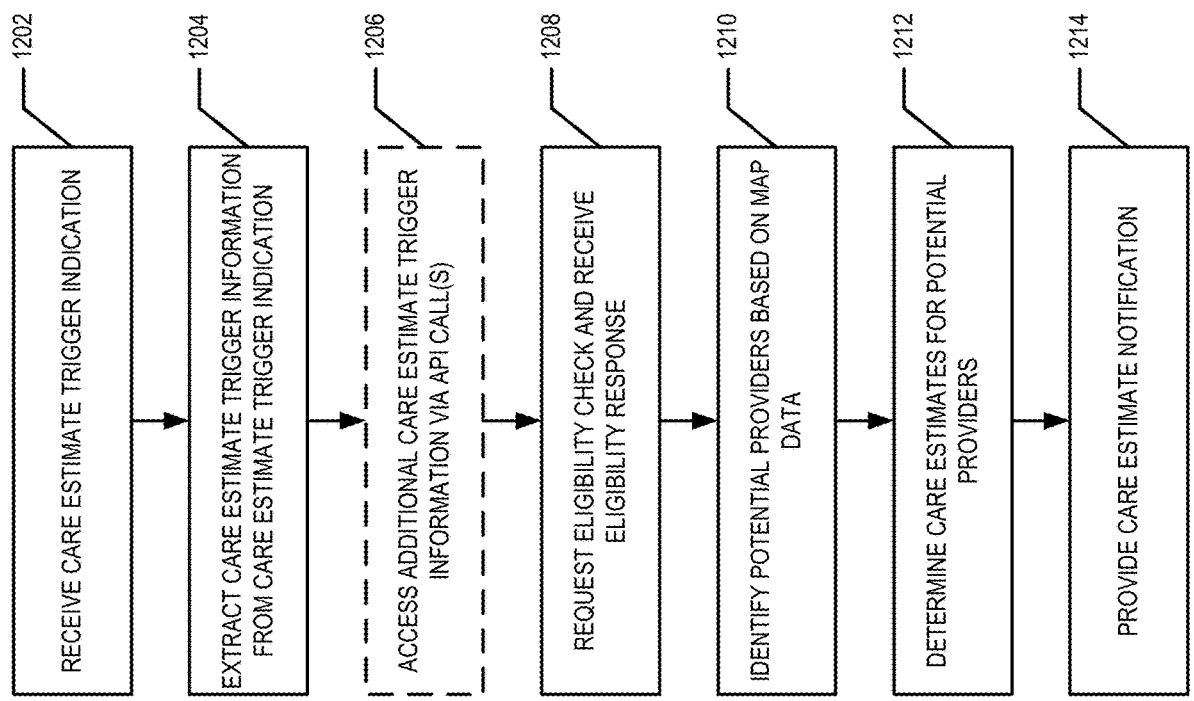
Figure 13:
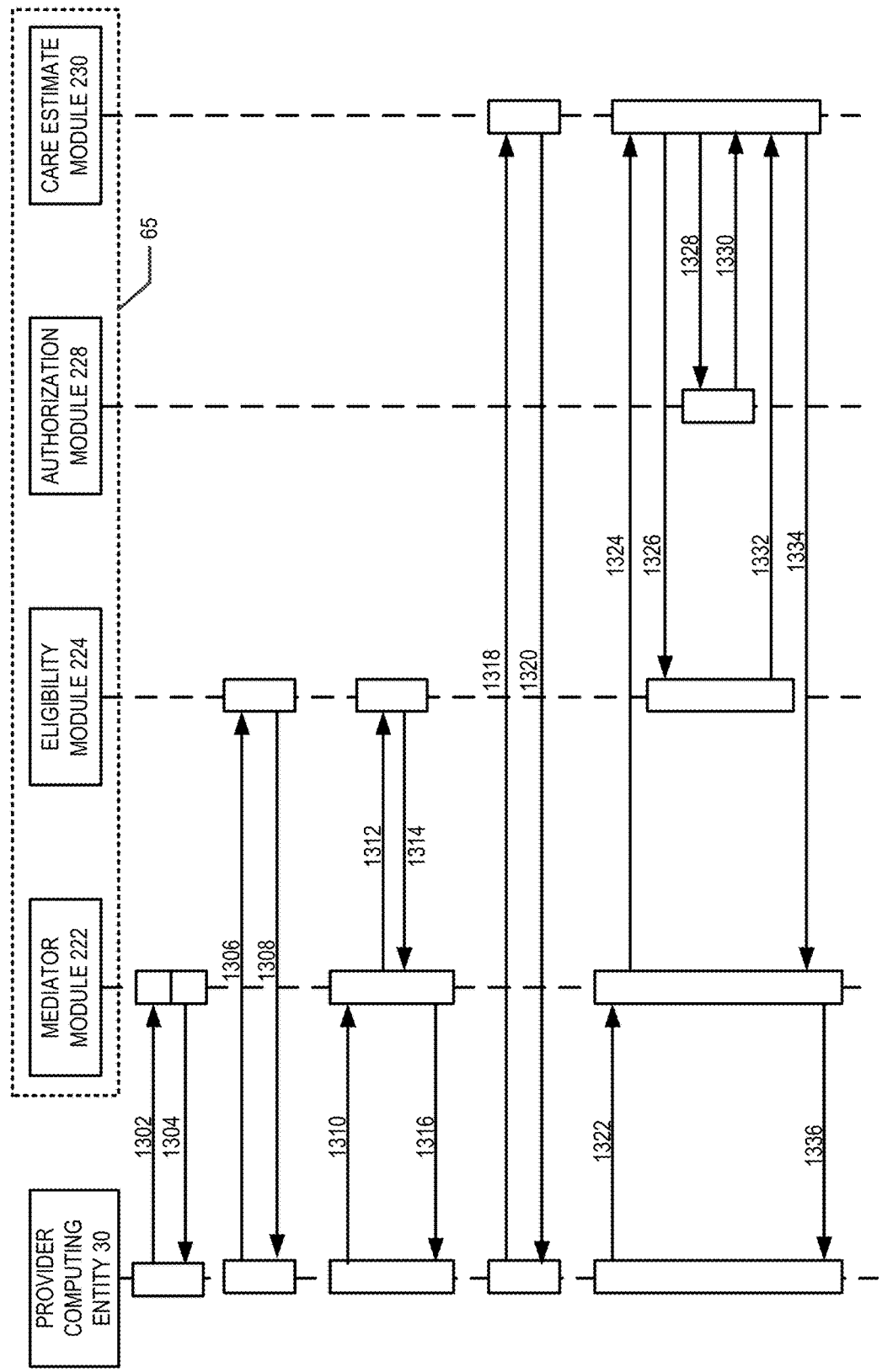
Figure 14:
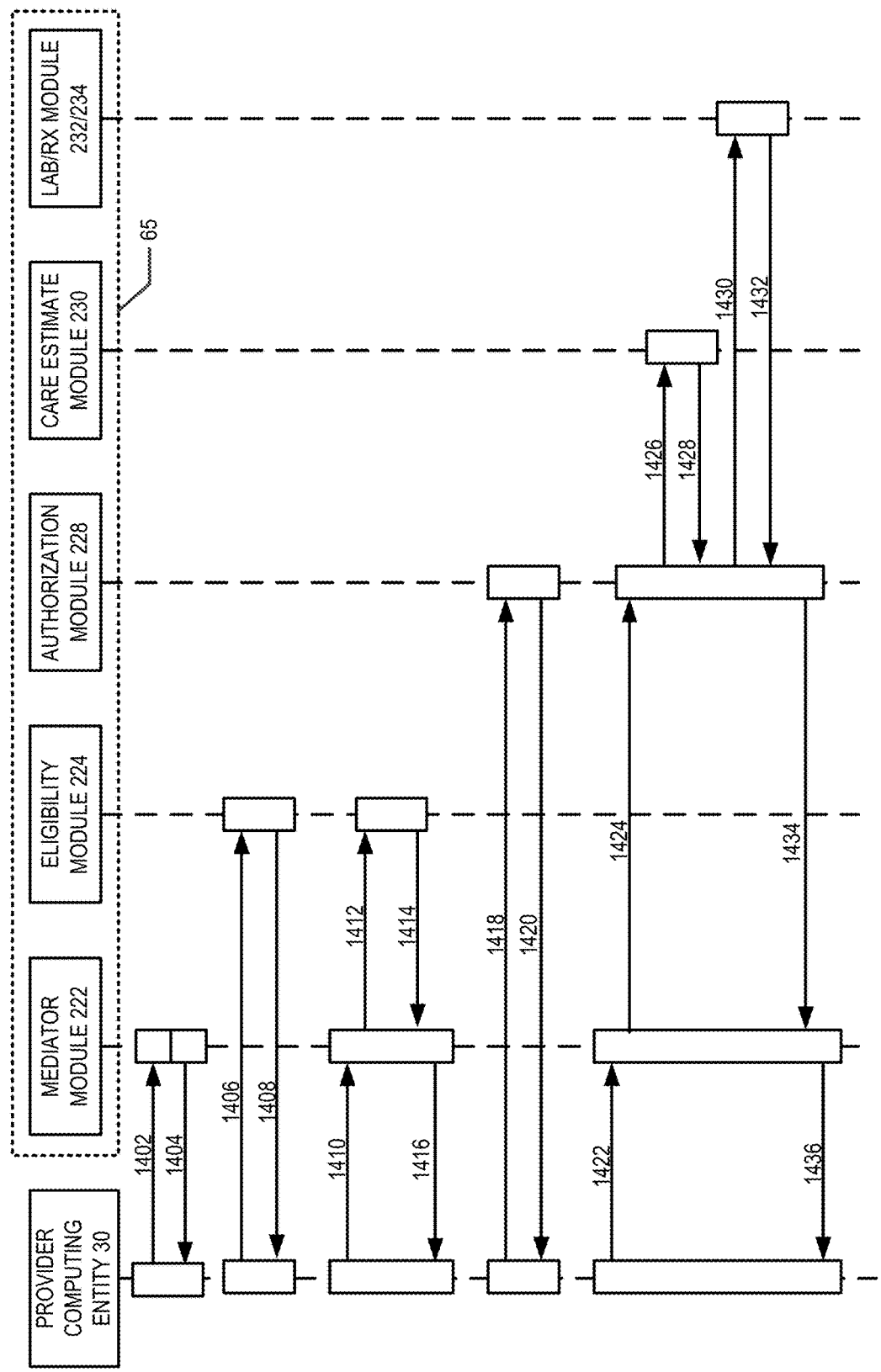

FIG. 4 provides an example view of an appointment scheduling user interface of an EMR and/or practice management system, in accordance with certain embodiments of the present invention;

FIG. 5 is a data flow diagram illustrating various processes, procedures, and/or operations performed to provide an eligibility confirmation, in accordance with certain embodiments of the present invention;

FIG. 6 provides a flowchart illustrating various processes, procedures, and/or operations for providing a care gap evaluation, in accordance with certain embodiments of the present invention;

FIG. 7 is a data flow diagram illustrating various processes, procedures, and/or operations performed to provide a care gap evaluation, in accordance with certain embodiments of the present invention;

FIG. 8 provides an example view of an appointment confirmation user interface of an EMR and/or practice management system including an eligibility confirmation and a care gap evaluation, in accordance with certain embodiments of the present invention;

FIG. 9 provides an example view of a care estimate evaluation user interface of an EMR and/or practice management system, in accordance with certain embodiments of the present invention;

FIG. 10 provides a patient chart view of a user interface of an EMR and/or practice management system, in accordance with certain embodiments;

FIG. 11 provides a care estimate request view of a user interface of an EMR and/or practice management system, in accordance with certain embodiments;

FIG. 12 provides a flowchart illustrating various processes, procedures, and/or operations for providing a care estimate evaluation, in accordance with certain embodiments of the present invention;

FIG. 13 is a data flow diagram illustrating various processes, procedures, and/or operations performed to provide a care estimate evaluation, in accordance with certain embodiments of the present invention; and FIG. 14 is a data flow diagram illustrating various processes, procedures, and/or operations performed to provide a care estimate evaluation corresponding to lab work or a prescription, in accordance with certain embodiments of the present invention.

DETAILED DESCRIPTION OF SOME EXAMPLE EMBODIMENTS

Various embodiments of the present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" (also designated as "/") is used herein in both the alternative and conjunctive sense, unless otherwise indicated. The terms "illustrative" and "exemplary" are used to be examples with no indication of quality level. Like numbers refer to like elements throughout.

I. Computer Program Products, Methods, and Computing Entities

Embodiments of the present invention may be implemented in various ways, including as computer program products that comprise articles of manufacture. Such computer program products may include one or more software components including, for example, software objects, methods, data structures, and/or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of a data structure, apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

II. Exemplary System Architecture

Figure 1:
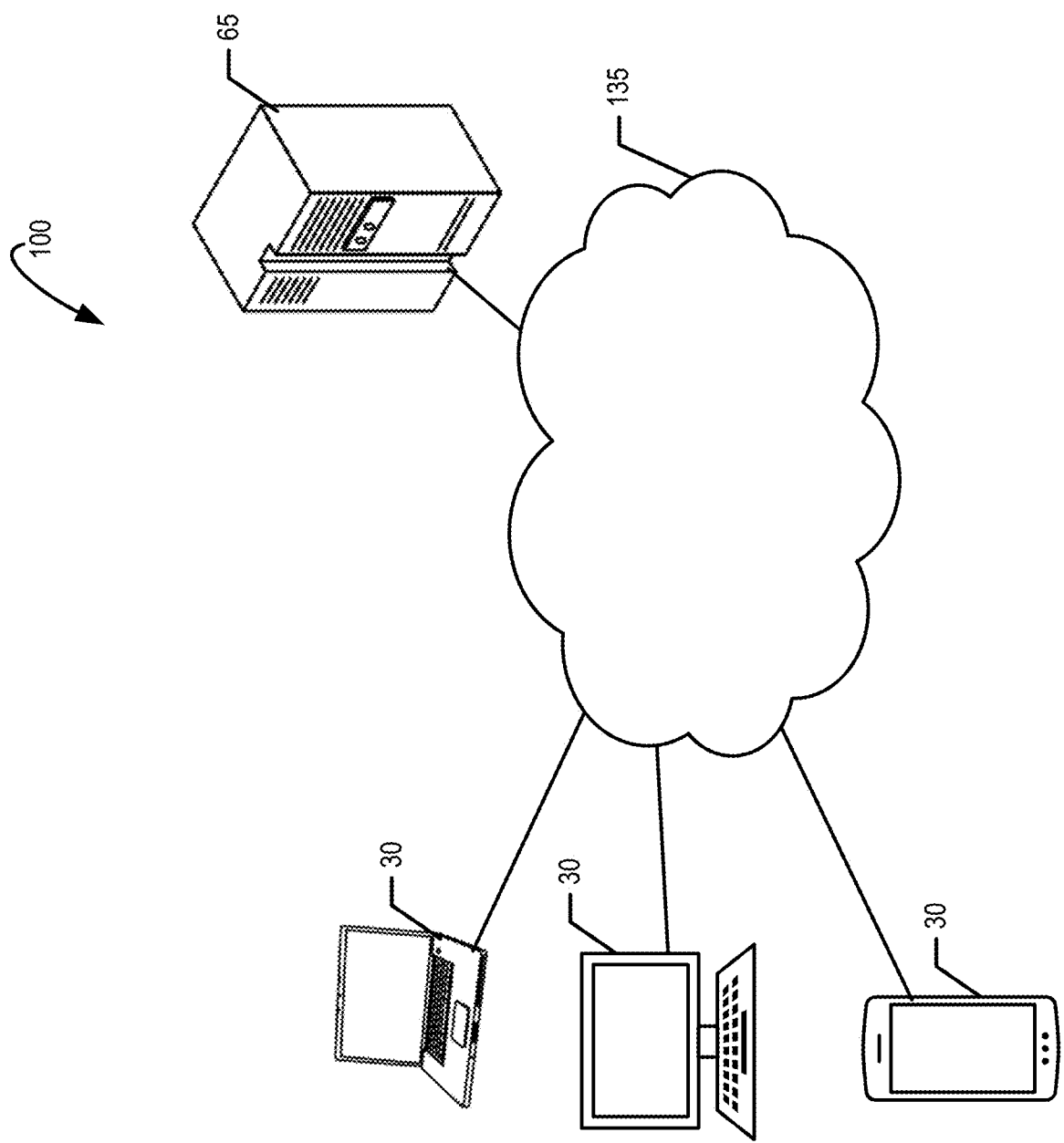
FIG. 1 is a diagram of a system that can be used in conjunction with various embodiments of the present invention.

FIG. 1 provides an illustration of a system 100 that can be used in conjunction with various embodiments of the present invention. As shown in FIG. 1, the system 100 may comprise one or more central computing entities 65, one or more user computing entities 30, one or more networks 135, and/or the like. In various embodiments, the one or more user computing entities 30 comprise provider computing entities and/or patient/member computing entities. Each of the components of the system may be in electronic communication with, for example, one another over the same or different wireless or wired networks 135 including, for example, a wired or wireless Personal Area Network (PAN), Local Area Network (LAN), Metropolitan Area Network (MAN), Wide Area Network (WAN), and/or the like. Additionally, while FIG. 1 illustrate certain system entities as separate, standalone entities, the various embodiments are not limited to this particular architecture.

a. Exemplary Central Computing Entity

Figure 2A:
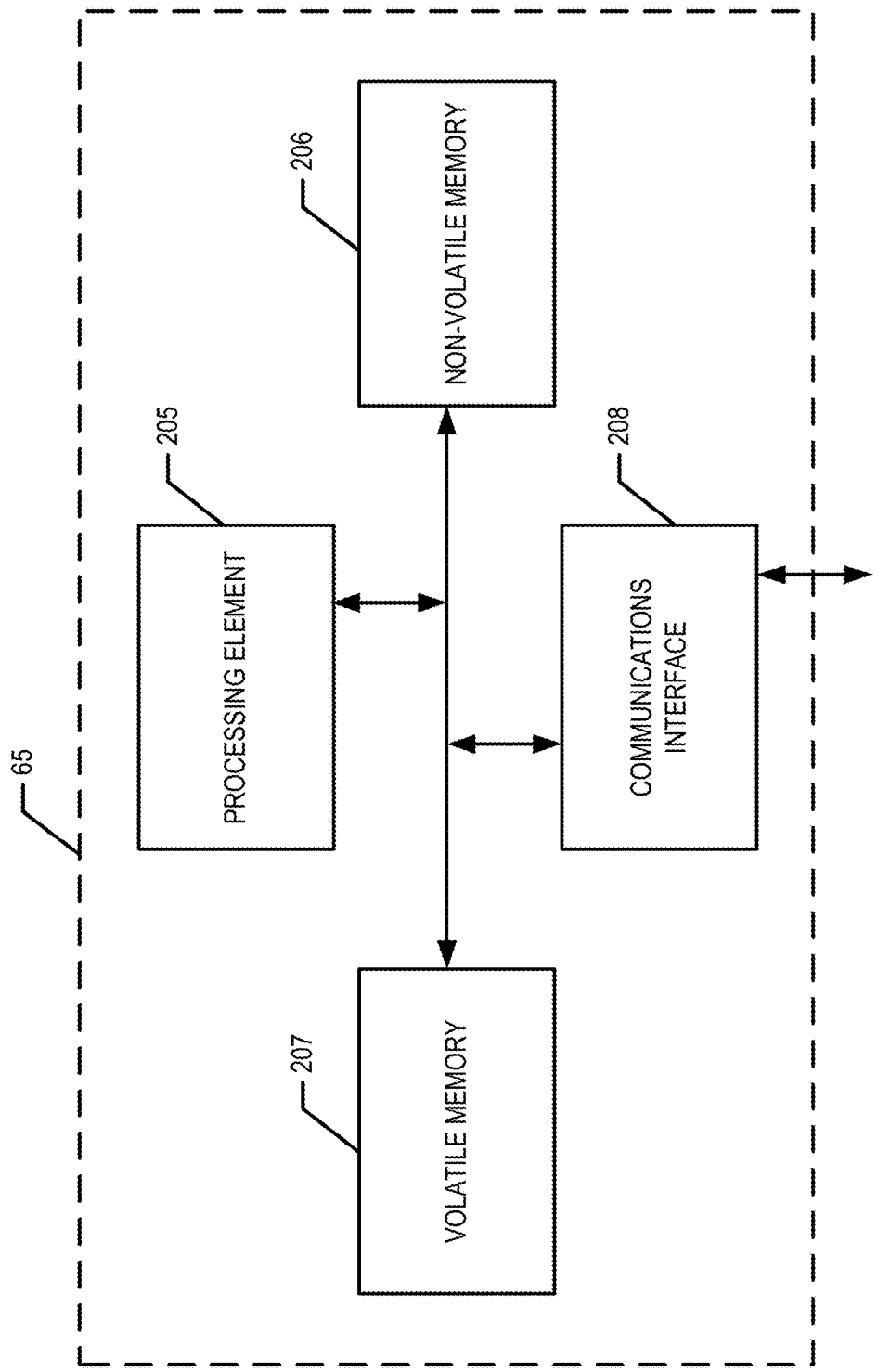
FIG. 2A is a schematic of a central computing entity in accordance with certain embodiments of the present invention.

FIG. 2A provides a schematic of a central computing entity 65 according to one embodiment of the present invention. In various embodiments, the central computing entity 65 executes one or more program modules, application program code, sets of computer executable instructions, and/or the like to provide back-end functionality that integrates with various EMR front-end and/or user-facing programs. In general, the terms computing entity, entity, device, system, and/or similar words used herein interchangeably may refer to, for example, one or more computers, computing entities, desktop computers, mobile phones, tablets, phablets, notebooks, laptops, distributed systems, items/devices, terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the central computing entity 65 may also include one or more network and/or communications interfaces 208 for communicating with various computing entities, such as by communicating data, content, information, and/or similar terms used herein interchangeably that can be transmitted, received, operated on, processed, displayed, stored, and/or the like. For instance, the central computing entity 65 may communicate with other computing entities, one or more user computing entities 30, and/or the like.

As shown in FIG. 2A, in one embodiment, the central computing entity 65 may include or be in communication with one or more processing elements 205 (also referred to as processors, processing circuitry, and/or similar terms used herein interchangeably) that communicate with other elements within the central computing entity 65 via a bus, for example, or network connection. As will be understood, the processing element 205 may be embodied in a number of different ways. For example, the processing element 205 may be embodied as one or more complex programmable logic devices (CPLDs), microprocessors, multi-core processors, coprocessing entities, application-specific instruction-set processors (ASIPs), and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

Figure 2B:
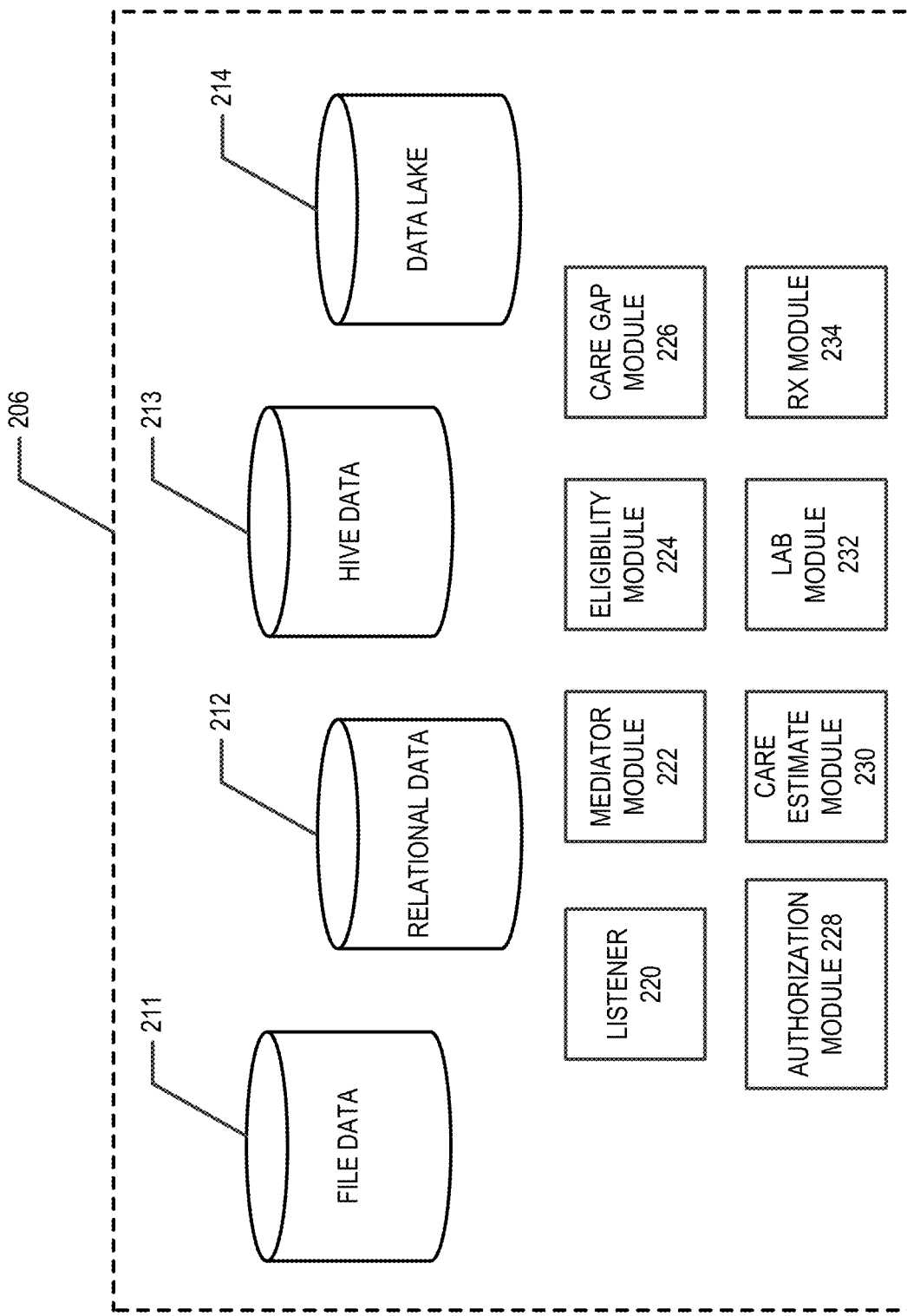
FIG. 2B is a schematic representation of a memory media storing a plurality of data assets.

In one embodiment, the central computing entity 65 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 206 as described above, such as hard disks, ROM, PROM, EPROM, EEPROM, flash memory, MMCs, SD memory cards, Memory Sticks, CBRAM, PRAM, FeRAM, RRAM, SONOS, racetrack memory, and/or the like. As will be recognized, the non-volatile storage or memory media may store databases, metadata repositories database instances, database management system entities, data, applications, programs, program modules, scripts, source code, object code, byte code, compiled code, interpreted code, machine code, executable instructions, and/or the like. For example, as shown in FIG. 2B, the memory media 206 may store computer executable code that, when executed by the processing element 205, causes the operation of a listener 220, mediator module 222, eligibility module 224, care gap module 226, authorization module 228, care estimate module 230, lab module 232, RX module 234, and/or the like, which are described in detail elsewhere herein. Though described as modules herein, the listener 220, mediator module 222, eligibility module 224, care gap module 226, authorization module 228, care estimate module 230, lab module 232, and/or RX module 234 may be embodied by various forms of computer-executable instructions, program/application code, and/or the like, in various embodiments. The term database, database instance, database management system entity, and/or similar terms used herein interchangeably and in a general sense to refer to a structured or unstructured collection of information/data that is stored in a computer-readable storage medium.

Memory media 206 (e.g., metadata repository) may also be embodied as a data storage device or devices, as a separate database server or servers, or as a combination of data storage devices and separate database servers. Further, in some embodiments, memory media 206 may be embodied as a distributed repository such that some of the stored information/data is stored centrally in a location within the system and other information/data is stored in one or more remote locations. Alternatively, in some embodiments, the distributed repository may be distributed over a plurality of remote storage locations only. An example of the embodiments contemplated herein would include a cloud data storage system maintained by a third party provider and where some or all of the information/data required for the operation of the system may be stored. As a person of ordinary skill in the art would recognize, the information/data required for the operation of the system may also be partially stored in the cloud data storage system and partially stored in a locally maintained data storage system.

Memory media 206 (e.g., metadata repository) may include information/data accessed and stored by the system to facilitate the operations of the system. More specifically, memory media 206 may encompass one or more data stores configured to store information/data usable in certain embodiments. For example, as shown in FIG. 2B, metadata for data assets may be stored in metadata repositories encompassed within the memory media 206. The metadata for the data assets in the metadata data stores, metadata repositories, and similar words used herein interchangeably may comprise file information/data 211, relational information/data 212, Hive information/data 213, data lake information information/data 214, and/or various other types of information/data. In an example embodiment, the memory media 206 may store patient/member data repositories, provider data repositories, care standard data repositories, and/or the like. As will be recognized, metadata repositories are inventories data assets in an organization's environment.

In one embodiment, the central computing entity 65 may further include or be in communication with volatile media (also referred to as volatile storage, memory, memory storage, memory circuitry and/or similar terms used herein interchangeably). In one embodiment, the volatile storage or memory may also include one or more volatile storage or memory media 207 as described above, such as RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. As will be recognized, the volatile storage or memory media may be used to store at least portions of the databases, database instances, database management system entities, data, applications, programs, program modules, scripts, source code, object code, byte code, compiled code, interpreted code, machine code, executable instructions, and/or the like being executed by, for example, the processing element 205. Thus, the databases, database instances, database management system entities, data, applications, programs, program modules, scripts, source code, object code, byte code, compiled code, interpreted code, machine code, executable instructions, and/or the like may be used to control certain aspects of the operation of the central computing entity 65 with the assistance of the processing element 205 and operating system.

As indicated, in one embodiment, the central computing entity 65 may also include one or more network and/or communications interfaces 208 for communicating with various computing entities, such as by communicating data, content, information, and/or similar terms used herein interchangeably that can be transmitted, received, operated on, processed, displayed, stored, and/or the like. For instance, the central computing entity 65 may communicate with computing entities or communication interfaces of other computing entities 65, user computing entities 30, and/or the like. In this regard, the central computing entity 65 may access various data assets.

As indicated, in one embodiment, the central computing entity 65 may also include one or more network and/or communications interfaces 208 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the central computing entity 65 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol. The central computing entity 65 may use such protocols and standards to communicate using Border Gateway Protocol (BGP), Dynamic Host Configuration Protocol (DHCP), Domain Name System (DNS), File Transfer Protocol (FTP), Hypertext Transfer Protocol (HTTP), HTTP over TLS/SSL/Secure, Internet Message Access Protocol (IMAP), Network Time Protocol (NTP), Simple Mail Transfer Protocol (SMTP), Telnet, Transport Layer Security (TLS), Secure Sockets Layer (SSL), Internet Protocol (IP), Transmission Control Protocol (TCP), User Datagram Protocol (UDP), Datagram Congestion Control Protocol (DCCP), Stream Control Transmission Protocol (SCTP), HyperText Markup Language (HTML), and/or the like.

As will be appreciated, one or more of the central computing entity's components may be located remotely from other central computing entity 65 components, such as in a distributed system. Furthermore, one or more of the components may be aggregated and additional components performing functions described herein may be included in the central computing entity 65. Thus, the central computing entity 65 can be adapted to accommodate a variety of needs and circumstances.

b. Exemplary User Computing Entity

Figure 3:
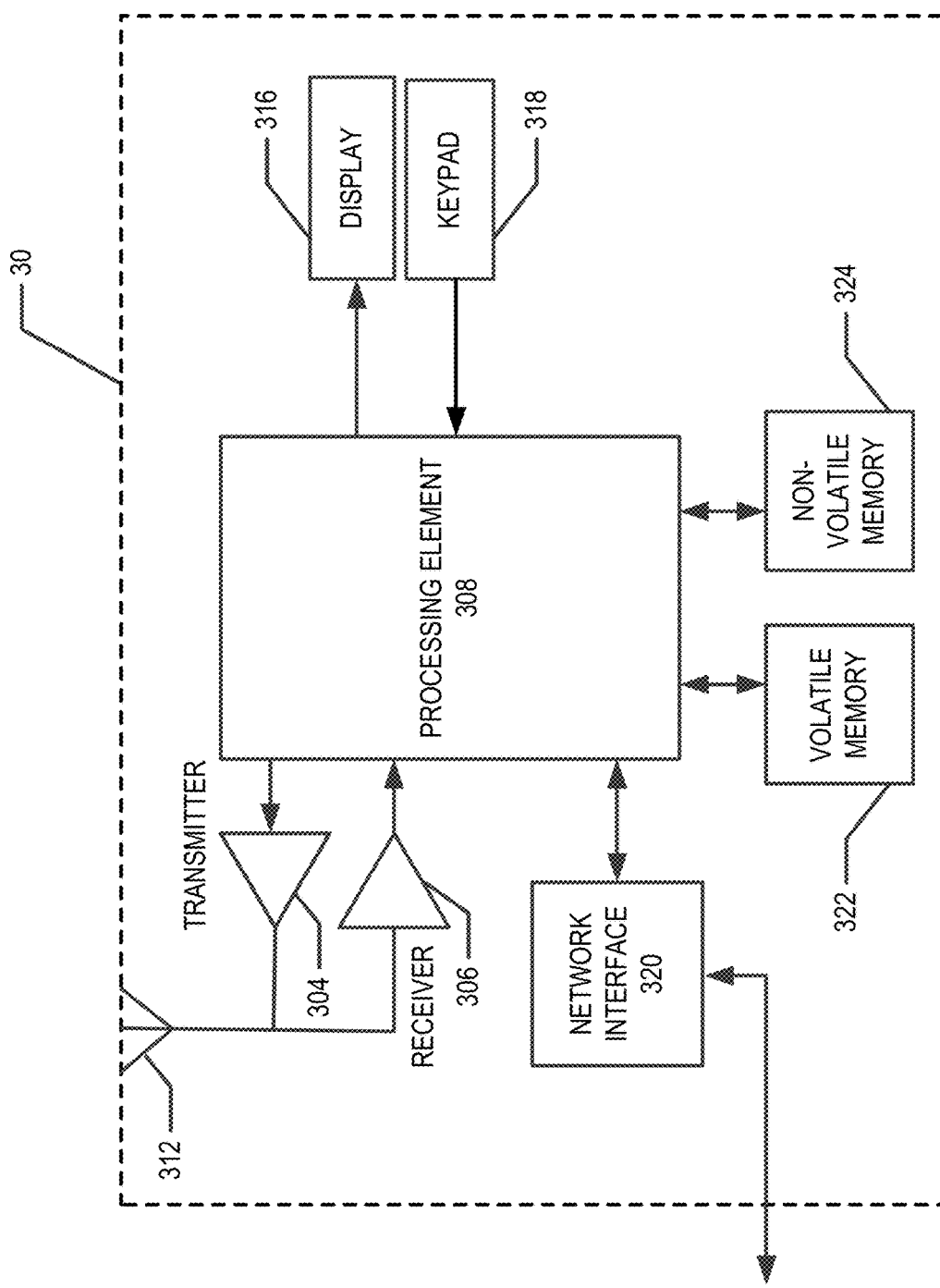
FIG. 3 is a schematic of a user computing entity in accordance with certain embodiments of the present invention.

FIG. 3 provides an illustrative schematic representative of user computing entity 30 that can be used in conjunction with embodiments of the present invention. In various embodiments, a user computing entity 30 may be a provider computing entity operated by and/or on behalf of a provider. In various embodiments, a provider is a healthcare provider; clinic; hospital; healthcare provider group; administrative and/or clinical staff associated with a healthcare provider, clinic, hospital, healthcare provider group, and/or the like; and/or other provider of healthcare services. In various embodiments, a provider computing entity operates and/or is in communication with (e.g., is a client, thin client, and/or the like) of a computing entity operating a front end and/or user-facing EMR program. In various embodiments, a user computing entity 30 is a patient/member computing entity. In various embodiments, a patient/member computing entity is operated by and/or on behalf of a patient and/or member of a policy, plan, and/or the like provided by an insurance company, payor, and/or other entity.

As will be recognized, the user computing entity may be operated by an agent and include components and features similar to those described in conjunction with the central computing entity 65. Further, as shown in FIG. 3, the user computing entity may include additional components and features. For example, the user computing entity 30 can include an antenna 312, a transmitter 304 (e.g., radio), a receiver 306 (e.g., radio) a network interface 320, and a processing element 308 that provides signals to and receives signals from the transmitter 304 and receiver 306, respectively. The signals provided to and received from the transmitter 304 and the receiver 306, respectively, may include signaling information/data in accordance with an air interface standard of applicable wireless systems to communicate with various entities, such as a central computing entity 65, another user computing entity 30, and/or the like. In this regard, the user computing entity 30 may be capable of operating with one or more air interface standards, communication protocols, modulation types, and access types. More particularly, the user computing entity 30 may operate in accordance with any of a number of wireless communication standards and protocols. In a particular embodiment, the user computing entity 30 may operate in accordance with multiple wireless communication standards and protocols, such as GPRS, UMTS, CDMA2000, 1×RTT, WCDMA, TD-SCDMA, LTE, E-UTRAN, EVDO, HSPA, HSDPA, Wi-Fi, WiMAX, UWB, IR protocols, Bluetooth protocols, USB protocols, and/or any other wireless protocol.

Via these communication standards and protocols, the user computing entity 30 can communicate with various other entities using concepts such as Unstructured Supplementary Service data (USSD), Short Message Service (SMS), Multimedia Messaging Service (MMS), Dual-Tone Multi-Frequency Signaling (DTMF), and/or Subscriber Identity Module Dialer (SIM dialer). The user computing entity 30 can also download changes, add-ons, and updates, for instance, to its firmware, software (e.g., including executable instructions, applications, program modules), and operating system.

According to one embodiment, the user computing entity 30 may include location determining aspects, devices, modules, functionalities, and/or similar words used herein interchangeably. For example, the user computing entity 30 may include outdoor positioning aspects, such as a location module adapted to acquire, for example, latitude, longitude, altitude, geocode, course, direction, heading, speed, UTC, date, and/or various other information/data. In one embodiment, the location module can acquire data, sometimes known as ephemeris data, by identifying the number of satellites in view and the relative positions of those satellites. The satellites may be a variety of different satellites, including LEO satellite systems, DOD satellite systems, the European Union Galileo positioning systems, the Chinese Compass navigation systems, Indian Regional Navigational satellite systems, and/or the like. Alternatively, the location information/data/data may be determined by triangulating the position in connection with a variety of other systems, including cellular towers, Wi-Fi access points, and/or the like. Similarly, the user computing entity 30 may include indoor positioning aspects, such as a location module adapted to acquire, for example, latitude, longitude, altitude, geocode, course, direction, heading, speed, time, date, and/or various other information/data. Some of the indoor aspects may use various position or location technologies including RFID tags, indoor beacons or transmitters, Wi-Fi access points, cellular towers, nearby computing devices (e.g., smartphones, laptops) and/or the like. For instance, such technologies may include iBeacons, Gimbal proximity beacons, BLE transmitters, Near Field Communication (NFC) transmitters, and/or the like. These indoor positioning aspects can be used in a variety of settings to determine the location of someone or something to within inches or centimeters.

The user computing entity 30 may also comprise a user interface comprising one or more user input/output devices/interfaces (e.g., a display 316 and/or speaker/speaker driver coupled to a processing element 308 and a touch screen, keyboard, mouse, and/or microphone coupled to a processing element 308). For example, the user output device/interface may be configured to provide an application, browser, interactive user interface (IUI), dashboard, webpage, Internet accessible/online portal, and/or similar words used herein interchangeably executing on and/or accessible via the user computing entity 30 to cause display or audible presentation of information/data and for user interaction therewith via one or more user input devices/interfaces. The user output interface may be updated dynamically from communication with the central computing entity 65. The user input device/interface can comprise any of a number of devices allowing the user computing entity 30 to receive information/data, such as a keypad 318 (hard or soft), a touch display, voice/speech or motion interfaces, scanners, readers, or other input device. In embodiments including a keypad 318, the keypad 318 can include (or cause display of) the conventional numeric (0-9) and related keys (#, *), and other keys used for operating the user computing entity 30 and may include a full set of alphabetic keys or set of keys that may be activated to provide a full set of alphanumeric keys. In addition to providing input, the user input device/interface can be used, for example, to activate or deactivate certain functions, such as screen savers and/or sleep modes. Through such inputs the user computing entity 30 can collect information/data, user interaction/input, and/or the like.

The user computing entity 30 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, RRAM, SONOS, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. The volatile and non-volatile storage or memory can store databases, database instances, database management system entities, data, applications, programs, program modules, scripts, source code, object code, byte code, compiled code, interpreted code, machine code, executable instructions, and/or the like to implement the functions of the user computing entity 30.

c. Exemplary Networks

In one embodiment, the networks 135 may include, but are not limited to, any one or a combination of different types of suitable communications networks such as, for example, cable networks, public networks (e.g., the Internet), private networks (e.g., frame-relay networks), wireless networks, cellular networks, telephone networks (e.g., a public switched telephone network), or any other suitable private and/or public networks. Further, the networks 135 may have any suitable communication range associated therewith and may include, for example, global networks (e.g., the Internet), MANs, WANs, LANs, or PANs. In addition, the networks 135 may include any type of medium over which network traffic may be carried including, but not limited to, coaxial cable, twisted-pair wire, optical fiber, a hybrid fiber coaxial (HFC) medium, microwave terrestrial transceivers, radio frequency communication mediums, satellite communication mediums, or any combination thereof, as well as a variety of network devices and computing platforms provided by network providers or other entities.

III. Technical Advantages

Various embodiments provide integrated back-end functionality to EMR and/or practice management systems. Some non-limiting examples of such integrated back-end functionality include eligibility checks, care gap checks, and care estimates. Various embodiments provide technical solutions to technical problems related to the processing of patient/member medical records, communication of patient/member medical information in a secure and private manner, and/or the like. An example technical problem addressed in various embodiments is that a central computing entity 65 may be in communication with a population of provider computing entities that are operating and/or associated with a plurality of EMR and/or practice management systems. In such embodiments, the central computing entity 65 is configured and/or programmed to provide back-end functionality that appears, from a user's view point, to be cohesive and/or tailored to each of the plurality of EMR and/or practice management systems. In an example embodiment, the back-end functionality is executed in a streamlined manner that is EMR and/or practice management system agnostic and a mediator module, program, application, and/or the like may translate and/or convert requests and responses/notifications between formats specific to EMR and/or practice management systems and the stream-lined format of the back-end functionality. Another technical problem addressed is the communication of patient/member medical information/data in a secure and private manner. Various embodiments of the present invention include authorization and/or authentication protocols and providing (e.g., transmission) of encrypted data to protect patient/member privacy.

Still another technical solution provided by various embodiments includes the automated identification of gaps in care for a patient/member in real-time or near real-time with respect to the triggering of a care gap check. Conventionally, care gap checks are performed manually and are based on patient/member medical information/data that is several months out-of-date. Conventionally, care gap checks are not be performed when the results of the care gap check may be timely put to use and patients/members are less motivated to use the results of such care gap checks because they are based on stale data. In the technical solution provided by various embodiments, the care gap check and the providing of a care gap evaluation may be performed using patient/member medical information/data that is up-to-date in real-time or near real-time with respect to the when the care gap check is triggered and/or performed. Such a care gap check may be triggered in real-time or near real-time with respect to multiple interaction points of the patient/member with the EMR and/or practice management system (e.g., when an appointment is scheduled; when the patient/member checks-in at the provider's location for the appointment; during in-take, check-out, or discharge of the patient/member from a provider's location; when a provider updates the patient/member medical information/data, and/or the like).

Yet another technical solution provided by various embodiments, includes the automated determination of cost estimates and provision of a care estimate evaluation. Conventionally, a provider may refer a patient/member for a service (e.g., order lab work, prescribe a prescription, order a test, and/or the like). However, if a patient/member is concerned about what their out-of-pocket cost for the service will be, the patient/member is significantly less likely to follow through on the care plan for the patient/member provided by the provider. Various embodiments provide an automated and accurate real-time or near real-time determination of a patient/member's out-of-pocket costs for a service for multiple providers that are conveniently located for the patient/member. Moreover, various embodiments provide the technical framework for allowing a cost estimate evaluation to be provided to a patient/member in response to a provider entering a referral for service into the EMR and/or practice management system and enables to patient/member to schedule the service.

Thus, various embodiments provide technical solutions to various technical problems related to providing integrated back-end functionality to EMR and/or practice management systems and providing automated EMR analysis via point of care computing systems.

IV. Exemplary System Operation

As described above, various embodiments provide integrated back-end functionality to various EMR and/or practice management systems. For example, a provider (e.g., healthcare provider, healthcare provider group, clinic, hospital, and/or the like) may use an EMR and/or practice management system to organize and/or store patient/member data and/or to schedule patient/member appointments. Administrative and/or clinical staff of the provider may access an IUI of the EMR and/or practice management system (e.g., via a user computing entity 30) to schedule patient/member appointments, check a patient/member in for an appointment, add new and/or changed patient/member information/data to a patient/member's EMR, and/or the like. In various embodiments, one or more components of the integrated back-end functionality may be triggered in response to user input received via the user computing entity 30. The central computing entity 65 may receive and/or identify a trigger indication corresponding to an integrated back-end functionality.

In various embodiments, the integrated back-end functionality is provided via widgets, pop-ups, and/or the like provided via an IUI of the EMR and/or practice management system. For example, a user (e.g., administrative and/or clinical staff and/or a patient/member) may access and/or make use of the integrated back-end functionality without leaving the IUI of the associated EMR and/or practice management system. Moreover, the integrated back-end functionality may be presented to the user such that the back-end functions (e.g., care gap evaluation, care estimate evaluation) is cohesive and/or aesthetically matched to the IUI of the EMR and/or practice management system. For example, various types of integrated back-end functionality may be accessed from a create/schedule new appointment IUI, patient/member check-in IUI, view patient/member chart, care estimator, prescription entry IUI, lab order IUI, referral entry IUI, patient/member check-out and/or discharge IUI, and/or other IUIs provided via the EMR and/or practice management system.

The central computing entity 65 may extract information/data from the trigger indication and/or access information/data via the EMR and/or practice management system or other data store (e.g., stored in memory media 206) and perform the triggered back-end function based on the extracted and/or accessed information/data. In various embodiments, extracted and/or accessed information/data may include patient/member information/data, some of which may be sensitive and/or protected information/data. Thus, various authentication, authorization, and/or encryption/decryption steps may be performed during the extracting and/or accessing of the information/data. Once the triggered back-end function has been performed, a result thereof (e.g., a care gap evaluation, care estimate evaluation, eligibility confirmation, and/or the like) may be provided to the user computing entity 30. In various embodiments, the central computing entity 65 may provide results of the performance of the triggered back-end functionality such that the security of any sensitive and/or protected information/data therein is maintained. The result, a portion thereof, and/or a graphical representation thereof may be provided through the IUI of the EMR and/or practice management system via the user computing entity 30. For example, the provider computing entity being operated by the administrative and/or clinical staff of the provider may display or audibly provide a result, a portion of a result, and/or a graphical representation of the result of the triggered back-end functionality. In another example, the central computing entity 65 and/or provider computing entity may cause a result, portion of a result and/or a graphical representation of the result of the triggered back-end functionality to be provided to patient/member via a patient/member computing entity (e.g., via SMS message, MMS message, instant message, email, an online portal, a dedicated application, and/or the like) for consumption and/or interaction therewith by the patient/member.

For example, the administrative and/or clinical staff operating the user computing entity 30 (e.g., a provider computing entity) may provide input (e.g., via a user input device/interface) selecting a selectable user interface element corresponding to a particular integrated back-end functionality. For example, an IUI of the EMR and/or practice management system may include a selectable element that a user may interact with (e.g., click, select, and/or the like) to trigger a corresponding back-end function such that the result of the back-end function is provided in a manner that is integrated with an IUI of the EMR and/or practice management system. For example, as shown in FIG. 4, an appointment scheduling IUI 400 of the EMR and/or practice management system that includes an eligibility check selectable element 408 and a care gap selectable element 410. In another example, FIG. 8 provides an example appointment confirmation IUI 800 of an EMR and/or practice management system comprising an eligibility confirmation 804 and care gap evaluation 806 that were provided via integrated back-end functions according to example embodiments. For example, user selection (e.g., by the administrative and/or clinical staff operating a provider computing entity) of the eligibility check selectable element 408 of the appointment scheduling IUI 400 shown in FIG. 4 may cause an integrated back-end functionality corresponding to an eligibility check to be triggered. In another example, user selection (e.g., by the administrative and/or clinical staff operating a provider computing entity) of the care gap selectable element 410 may cause an integrated back-end functionality corresponding to a care gap evaluation to be triggered. For example, user selection of an eligibility check selectable element 408 and/or care gap selectable element 410 may cause the provider computing entity to generate and provide a corresponding trigger indication and provide/submit the trigger indication to the central computing entity 65 for performance of the corresponding back-end functionality.

In an example embodiment, a listener 220 operating on the central computing entity 65 and/or a provider computing entity may identify a trigger and automatically generate trigger indications for one or more integrated back-end functions. For example, when a user provides input selecting the submit selectable element 412 of the appointment scheduling IUI 400, the listener 220 may determine that an appointment is being scheduled and may automatically generate trigger indications for an eligibility check and/or care gap evaluation corresponding to the appointment being scheduled. In an example embodiment, CDS hooks are used to trigger and/or cause the automatic generation of a trigger indication for one or more integrated back-end functions.

In various embodiments, a trigger indication may comprise trigger information/data. In various embodiments, the trigger information/data may include identifying information/data identifying the corresponding patient/member (e.g., patient identifier configured to uniquely identify the patient/member, patient/member name, patient/member birth date, patient/member address, and/or the like), patient/member insurance policy information/data (e.g., plan number, group number, and/or the like), trigger cause information/data (e.g., what caused the trigger indication to be generated—an appointment being scheduled; a patient being checked in at a provider's office, clinic, hospital, and/or other facility; labs or test being ordered; a prescription being prescribed; information/data of the patient/member's EMR being added to and/or updated; a patient being released/discharged from a clinic, hospital, or other facility; a threshold amount of time having passed since the back-end functionality was performed for the patient/member; and/or the like), current medical information/data for the patient/member (e.g., current symptoms, in text or standardized medical codes), historical medical information/data for the patient/member (e.g., medical information/data stored in the EMR corresponding to the patient/member), an indication of which back-end function(s) are being triggered, a type and/or version of the EMR and/or practice management system corresponding to and/or being operated by the provider computing entity, authentication and/or authorization information/data for the provider, and/or the like. The central computing entity 65 (e.g., a mediator module 222 operating on the central computing entity 65) may receive the trigger indication, perform authentication and/or authorization functions, and extract information/data provided in the trigger indication. The central computing entity 65 may then (e.g., via the mediator module 222) access any additional information/data required for performance of the triggered back-end functionality indicated in the trigger indication. For example, the mediator module 222 may issue one or more application program interface (API) calls to one or more APIs exposed by the EMR and/or practice management system and/or access information/data stored in memory media 206. In various embodiments, the communications between user computing entities 30 (e.g., provider computing entities and/or patient/member computing entities) and/or EMR and/or practice management systems operating thereon and a central computing entity 65 (e.g., a mediator module 222, eligibility module 224, care gap module 226, authorization module 228, care estimate module 230, and/or the like operating on the central computing entity 65) uses Fast Healthcare Interoperability Resources (FHIR) communication protocols. For example, the mediator module 222 may issue one or more FHIR API calls to access information/data corresponding to a patient/member and/or to provide a notification to a provider computing entity.

The mediator module 222 may then communicate with one or more other modules to perform one or more triggered back-end functionalities. For example, the mediator module 222 may communicate with an eligibility module 224 to check and/or confirm the patient/member's eligibility (e.g., that the patient/member has a current plan, what the patient/member's current plan is, and/or the like). In another example, the mediator module 222 may communicate with a care gap module 226 to identify any gaps in care in the patient/member's medical care, history, and/or the like. In another example, the mediator module 222 may communicate with an authorization module 228 to determine if the patient/member is pre-authorized for one or more labs, tests, prescriptions, operations, therapies, office visits, care events, and/or the like. In another example, the mediator module 222 may communicate with a care estimate module 230 to identify one or more providers that may be able to provide a patient/member with recommended/required service (e.g., imaging services, specialists, and/or the like), performance of a test or lab work, prescription, and/or the like and determine an estimate for the recommended/required service, performance of the test or lab work, prescription, and/or the like for the patient/member. For example, the mediator module 222 may communicate with a lab module 232 configured to interface with one or more lab computing entities each corresponding to a lab that performs lab work to determine appointment availability, services provided, costs for services provided for various patients/members (e.g., based on the patient/member's current plan), and/or submit lab work orders. For example, the mediator module 222 may communicate with a RX module 234 configured to communicate with one or more pharmacy computing entities each corresponding to a pharmacy to determine availability of one or more prescriptions, cost of a prescription for a patient/member (e.g., based on the patient/member's current plan), submit a prescription to a pharmacy, and/or the like.

Once the mediator module 222 receives results from the performance of each of the one or more triggered back-end functionalities, the mediator module 222 may cause the central computing entity 65 to provide at least a portion of the result and/or representation thereof. A user computing entity 30 (e.g., provider computing entity and/or patient/member computing entity) may receive the result, portion of the result, and/or representation of the result and provide the result, a portion of the result, and/or a graphical representation thereof via a user interface of the user computing entity 30 (e.g., via the IUI of the EMR and/or practice management system, SMS message, MMS message, instant message, email, an online portal, a dedicated application, and/or the like).

As should be understood, various integrated back-end functionalities may be provided by the central computing entity 65 to a variety of EMR and/or practice management systems operating on one or more provider computing entities. Various features of various embodiments will now be described in relation to some example integrated back-end functionalities.

For example, administrative and/or clinical staff corresponding to a provider may access an appointment scheduling IUI 400 of the EMR and/or practice management system via a provider computing entity, an example of which is provided in FIG. 4. The administrative and/or clinical staff may operate the provider computing entity provide (e.g., via user input device(s)/interface(s)) identifying information/data identifying a patient/member that is scheduling an appointment in patient/member identifying fields 402 of the appointment scheduling IUI 400. The administrative and/or clinical staff may operate the provider computing entity to select a reason/description of the appointment being scheduled via the appointment type element 404 and/or select a date and time for the appointment via the appointment date/time elements 406. In various embodiments, the administrative and/or clinical staff may select (e.g., via a user input device/interface) the eligibility check selectable element 408, care gap selectable element 410, or submit selectable element 412. User selection of the eligibility check selectable element 408 and/or the submit selectable element 412 may cause (e.g., either directly or via a listener 220) the generation of a trigger indication and the passing of the trigger indication to the mediator module 222.

FIG. 5 illustrates an example data flow between a provider computing entity (e.g., an EMR and/or practice management system operating on the provider computing entity) and a mediator module 222 and an eligibility module 224 operating on a central computing entity 65. For example, the provider computing entity (e.g., as caused by the EMR and/or practice management system operating on the provider computing entity) provides (e.g., transmits) an authorization and/or authentication request 502 (e.g., comprising authorization, authentication, and/or credentialing information/data and/or other information/data identifying and/or confirming the identity of the provider). The mediator module 222 operating on the central computing entity 65 receives and analyzes the authorization and/or authentication request and provides an authentication and/or authorization response 504. For example, the authentication and/or authorization response 504 may include an authorization token (e.g., an Oauth token, in an example embodiment). The provider computing entity (e.g., as caused by the EMR and/or practice management system) receives the authentication and/or authorization response 504. The provider computing entity (e.g., as caused by the EMR and/or practice management system operating on the provider computing entity) may then provide (e.g., transmit) an eligibility authorization and/or authentication request 506 (e.g., comprising authorization and/or authentication information/data and/or the authorization token). The eligibility module 224 operating on the central computing entity 65 receives and analyzes the eligibility authorization and/or authentication request 506 and provides an eligibility authentication and/or authorization response 508. In an example embodiment, the eligibility module 224 links the authorization token to a particular transaction, set of authorization capabilities, and/or the like. The provider computing entity (e.g., as caused by the EMR and/or practice management system) receives the eligibility authentication and/or authorization response 508.

The provider computing entity (e.g., as caused by the EMR and/or practice management system operating thereon) may then provide (e.g., transmit) an eligibility request 510. For example, the mediator module 222 may receive the eligibility request 510. In various embodiments, the eligibility request 510 includes patient/member identifying information/data, the authorization token, information/data identifying the provider, an indication of the appointment type and/or reason, and/or the like. In various embodiments, the mediator module 222 may check the authorization token to ensure that the provider corresponding to the eligibility request 510 is authorized, authenticated, and/or appropriately credentialed to receive eligibility information/data responsive to the eligibility request 510. After and/or responsive to the mediator module 222 determines that the provider corresponding to the eligibility request 510 is authorized, authenticated, and/or appropriately credentialed to receive eligibility information/data responsive to the eligibility request 510, the mediator module 222 may reformat the eligibility request 510 and/or translate the eligibility request 510 to generate an eligibility inquiry 512. For example, the eligibility inquiry 512 may be an eligibility and/or benefits 270 inquiry. For example, various EMR and/or practice management systems may generate and provide eligibility requests having a variety of formats. The mediator module 222 may be configured and/or programmed to convert and/or translate the eligibility request 510 into a standardized eligibility inquiry 512 format. In an example embodiment, the eligibility inquiry 512 may be in JSON, SQL, and/or other data interchange format. The mediator module 222 may then provide the eligibility inquiry 512.

The eligibility module 224 may receive the eligibility inquiry 512. Responsive to receiving and/or reading the eligibility inquiry 512, the eligibility module 224 may use the patient/member identifying information/data to identify eligibility information/data corresponding to the identified patient/member in a patient/member data repository (e.g., file information/data 211, relational information/data 212, Hive information/data 213, data lake information information/data 214, a patient/member database, and/or the like). The eligibility module 224 may read the eligibility information/data from the patient/member data repository corresponding to the patient/member identified by the identifying information/data of the eligibility inquiry 512, and generate an eligibility response 514 based thereon. In various embodiments, generating the eligibility response 514 may comprise making one or more determinations based on the information/data provided in the eligibility inquiry 512 and eligibility information/data read from the patient/member data repository. For example, generating the eligibility response 514 may comprise analyzing information/data provided in the eligibility inquiry 512 based on the eligibility information/data read from the patient/member data repository. For example, the eligibility response 514 may comprise the identifying information/data identifying the patient/member, an indication of whether or not the patient/member is eligible for an appointment of the appointment type with the provider, a transaction identifier corresponding to the transaction of checking the patient/member eligibility, and/or the like. In various embodiments, the eligibility inquiry 512 is in JSON or another data interchange format. The eligibility module 224 may then provide the eligibility response 514. In an example embodiment, the eligibility response is an eligibility and/or benefits response 271.

The mediator module 222 may receive the eligibility response 514 and may convert and/or translate the eligibility response 514 into an eligibility confirmation 516. For example, in various embodiments, the mediator module 222 may convert and/or translate the eligibility request 514 into a format corresponding to the EMR and/or practice management system in communication with and/or being operated by the provider computing entity. For example, the eligibility request 510 may include an indication of the EMR and/or practice management system in communication with and/or being operated by the provider computing entity and the conversion and/or translation of the eligibility request 510 to the eligibility inquiry 512 and/or conversion and/or translation of the eligibility response 514 to the eligibility confirmation 516 may be based at least in part on the EMR and/or practice management system in communication with and/or operating on the provider computing entity. The provider computing entity may receive, read, and/or analyze the eligibility confirmation 516 and provide and/or display an eligibility confirmation 804. For example, the eligibility confirmation 804 may be provided and/or displayed via an appointment confirmation IUI 800 (an example view of which is provided in FIG. 8).

In various embodiments, the checking of the patient/member's eligibility may be performed as part of and/or responsive to scheduling of an appointment, as part of performing/providing a care gap evaluation, as part of performing/providing a care estimate evaluation, as part of and/or responsive to checking the patient/member in for an appointment, as part of and/or responsive to checking the patient/member out after an appointment, as part of and/or responsive to in-take and/or discharging of the patient/member, as part of updating and/or adding to an EMR corresponding to the patient/member, and/or other time the EMR corresponding to the patient/member is accessed.

As should be understood, the patient/member may access an appointment scheduling IUI 400 via a patient/member computing entity. For example, the patient/member may access the appointment scheduling IUI 400 via a dedicated application, a web browser, online portal, and/or the like. The appointment confirmation, eligibility confirmation, care gap evaluation, care estimate evaluation, and/or the like may be provided to the patient/member computing entity and/or the provider computing entity. For example, the patient/member computing entity and/or the provider computing entity may provide and/or display an appointment confirmation IUI 800, an example view of which is shown in FIG. 8.

Some additional examples of integrated back-end functionalities will now be described.

a. Exemplary Care Gap Evaluation

In various embodiments, an example back-end function provided via the integrated back-end functionality is a care gap evaluation. For example, based on a patient/member's medical history, as summarized and/or described in the patient/member's EMR, a care gap module 226 may determine if any gaps in care are present in the patient/member's medical history and, if one or more gaps in care are present in the patient/member's medical history, identify the gaps in care.

In various embodiments, the integrated back-end functionality of a care gap check, resulting in the providing of a care gap evaluation, may be performed responsive to administrative and/or clinical staff associated with a provider and/or a patient/member (and/or an agent thereof) selecting a care gap selectable element 410 (e.g., using a user input device/interface) via an IUI associated with the EMR and/or practice management system of the provider. In an example embodiment, a listener 220 may be operating on the central computing entity 65 and/or provider computing entity and determine when an EMR corresponding to a patient/member is accessed, modified, updated, and/or the like and/or when another function of the EMR and/or practice management system corresponding to the patient/member is performed (e.g., the patient/member is scheduled for an appointment, the patient/member is checked in for an appointment, and/or the like). For example, a trigger indication may be generated and/or provided that triggers the performance of a care gap check for a patient/member (resulting in the providing of a care gap evaluation for the patient/member) in response to user input received via an IUI associated with the EMR and/or practice management system (e.g., through user interaction with a user input device/interface) and/or a listener 220 identifying the accessing, modifying, and/or the like of an EMR corresponding to the patient/member.

In various embodiments, performing a care gap check may include analyzing at least a portion of the patient/member's medical history (as described and/or summarized by the EMR corresponding to the patient/member) based on one or more care standards that are relevant and/or applicable to the patient/member. For example, one or more care standards may be defined and stored in a data repository (e.g., stored by memory media 206). A care standard may be associated with relevancy information/data. For example, a first care standard may be associated with relevancy information/data indicating the that the first care standard is relevant and/or applicable to any patient/member independent of the patient/member's demographics or medical history. A second care standard may be associated with relevancy information/data indicating that the second care standard is relevant and/or applicable to any patient/member that is female and over the age of 50. A third care standard may be associated with relevancy information/data indicating that the third care standard is relevant and/or applicable to patients/members with a particular medical history (e.g., the EMR corresponding to the patient/member includes one or more particular diagnosis codes, intervention codes, prescription codes, procedure codes, and/or other medical codes). In another example, a fourth care standard may be associated with relevancy information/data indicating that the fourth care standard is relevant and/or applicable to patients/members who are black men in the age range of 20-40 and having a particular medical history (e.g., the EMR corresponding to the patient/member includes one or more particular diagnosis codes, intervention codes, prescription codes, procedure codes, and/or other medical codes). Thus, a care standard may be associated with relevancy information/data that indicates that the care standard is relevant and/or applicable to patients/members of a particular demographic (e.g., age, sex, race, geographic location, and/or the like) and/or having a particular medical history.

In various embodiments, a care standard indicates one or more procedures, lab work, tests, and/or the like that a patient/member's medical history should include and a frequency with which each procedure, lab work, test, and/or the like should be present in the patient/member's medical history. For example, a care standard may be associated with relevancy information/data that indicates that the care standard is relevant and/or applicable to patients/members that are currently taking drug X and indicate that a patient/member currently taking drug X should have lab work done on a yearly basis that includes a particular liver test to ensure proper functioning of the patient/member's liver. In an example embodiment, a care gap check includes identifying one or more care standards that apply and/or are relevant to a patient/member (e.g., based on the patient/member's medical history and/or demographic information/data) and analyzing the patient/member's medical history based at least in part on each of the identified applicable and/or relevant care standards. For example, performing a care gap check may include identifying any procedures, lab work, tests, and/or the like that, according to one or more care standards that are relevant and/or applicable to the patient/member, that should have been performed, but have not been performed. For example, if the patient/member is currently taking drug X, as indicated by the patient/member's EMR, and the EMR corresponding to the patient/member does not include lab work including a test to test the functioning of the patient/member's liver within the past twelve months, a care gap may be identified. For example, the identified care gap may be that the patient/member has not had lab work including the test to test the patient/member's liver function within the past twelve months (e.g., the last set of lab work that included the test to test the patient/member's liver function was performed 14 months ago) and should be performed. A procedure may include a therapy, an imaging procedure, an inpatient procedure, an outpatient procedure, a screening, and/or the like.

FIG. 6 provides a flowchart illustrating various processes, procedures, operations, and/or the like performed by a central computing entity 65 to generate and/or provide a care gap evaluation. For example, a patient/member may operate a patient/member computing entity (which is an example of a user computing entity 30) and/or administrative and/or clinical staff associated with a provider may operate a provider computing entity (which is another example of a user computing entity 30) to interact with an IUI associated with an EMR and/or practice management system operated by and/or on behalf of the provider and/or to otherwise provide input to the EMR and/or practice management system. For example, the patient/member and/or administrative and/or clinical staff may provide user input (e.g., via a user input device/interface of a user computing entity 30) to schedule an appointment for the patient/member; check in the patient/member for an appointment; order labs or test for the patient/member; prescribe a prescription to the patient/member; add and/or update information/data of the patient/member's EMR; release/discharge the patient/member from a clinic, hospital, or other facility; select a care gap check selectable element 410 of the IUI; and/or the like. In response to receiving the user input (and/or a threshold amount of time having passed since a care gap trigger indication corresponding to the patient/member was generated and/or provided) the EMR and/or practice management system (e.g., operating on the provider computing entity) and/or a listener 220 (e.g., operating on the central computing entity 65 and/or the provider computing entity) may generate a care gap trigger indication. The care gap trigger indication may then be provided (e.g., by the listener 220 and/or the EMR and/or practice management system) such that the mediator module 222 receives the care gap trigger indication.

At step/operation 602, the care gap trigger indication is received. For example, the mediator module 222 operating on the central computing entity 65 may receive the care gap trigger indication. In various embodiments, the care gap trigger indication comprises trigger information/data. In various embodiments, the trigger information/data includes identifying information/data identifying the corresponding patient/member (e.g., patient identifier configured to uniquely identify the patient/member, patient/member name, patient/member birth date, patient/member address, and/or the like), patient/member insurance policy information/data (e.g., plan number, group number, and/or the like), trigger cause information/data (e.g., what caused the trigger indication to be generated—an appointment being scheduled; a patient being checked in at a provider's office, clinic, hospital, and/or other facility; labs or test being ordered; a prescription being prescribed; information/data of the patient/member's EMR being added to and/or updated; a patient being released/discharged from a clinic, hospital, or other facility; a threshold amount of time having passed since the back-end functionality was performed for the patient/member; and/or the like), current medical information/data for the patient/member (e.g., current symptoms, in text or standardized medical codes), historical medical information/data for the patient/member (e.g., medical information/data stored in the EMR corresponding to the patient/member), an indication that a care gap check has been triggered, a type and/or version of the EMR and/or practice management system corresponding to and/or being operated by the provider computing entity, authentication and/or authorization information/data for the provider, and/or the like.

At step/operation 604, at least some of the trigger information/data is extracted from the care gap trigger indication. For example, the mediator module 222 (and/or the care gap module 226) operating on the central computing entity 65 may extract at least some of the trigger information/data from the care gap trigger indication. The care gap module 226 may receive the extracted trigger information/data and determine if any other information/data is needed for identifying one or more care standards relevant and/or applicable to the patient/member identified in the trigger indication and determining if the patient/member's EMR is complete (e.g., based on the identified one or more care standards) and/or determining if the patient/member's EMR has one or more care gaps (e.g., based on the identified one or more care standards). At step 606, the care gap module 226 may request and receive any additional information/data (e.g., in addition to the information/data extracted from the care gap trigger indication). For example, the care gap module 226 may issue one or more API calls to access information/data stored by the EMR and/or practice management system and/or in a patient/member data repository. In an example embodiment, the care gap module 226 may determine which API calls to issue based at least in part on the type and/or version of the EMR and/or practice management system corresponding to and/or being operated by the provider computing entity extracted from the care gap trigger indication. For example, the API calls issued may be for one or more APIs exposed by and/or associated with the on the type and/or version of the EMR and/or practice management system indicated by the care gap trigger indication.

At step/operation 608, eligibility information/data may be requested and received. For example, the care gap module 226 may request eligibility information/data for the patient/member from the eligibility module 224. For example, the care gap module 226 may generate and provide an eligibility check request comprising identifying information/data for the patient/member. The eligibility module 224 may receive the eligibility check request, access eligibility information/data corresponding to the patient/member, and provide the eligibility information/data. The care gap module 226 may then receive the eligibility information/data.

At step operation 610, the care gap module 226 may perform the care gap check. For example, based on the patient/member's medical history and/or demographics, the care gap module 226 may identify one or more care standards that are relevant and/or applicable to the patient/member and determine if the patient/member's medical history (e.g., as represented by the patient/member's EMR and/or information/data extracted from the care gap trigger indication at step/operation 604 and/or requested and received at step/operation 606). In an example embodiment, one or more API calls may be issued to access information/data corresponding to the patient/member prior to identifying the one or more care standards that are relevant and/or applicable to the patient/member and one or more API calls are issued after identifying the one or more care standards that are relevant and/or applicable to the patient/member. For example, the care gap module 226 may request information/data corresponding to demographic information/data corresponding to the patient/member and/or request medical history information/data corresponding to the patient/member that may be used to identify one or more care standards that are relevant and/or applicable to the patient/member. The care gap module 226 may then request medical history information/data corresponding to the patient/member based on the one or more identified care standards that are relevant and/or applicable to the patient/member. For example, if a care standard indicates that a patient/member should have a particular test performed at a particular frequency, the care gap module 226 may request medical history information/data corresponding to the patient/member indicating when the patient/member last had the particular test was performed.

Thus, the care gap module 226 may identify any gaps in the patient/member's medical history (e.g., as indicated by the EMR corresponding to the patient/member). In various embodiments, a gap in the patient's medical history is identified when a care standard identified as being relevant and/or applicable to the patient/member indicates that the patient/member should have had a particular procedure, lab work, test, and/or the like performed within a particular time window (e.g., determined based on a frequency indication of the car standard) and the particular procedure, lab work, test, and/or the like was not performed within the particular time window. The care gap module 226 may then generate a care gap notification. In various embodiments, the care gap notification indicates whether or not any gaps in the patient/member's medical history were found. In an example embodiment, when one or more gaps in the patient/member's medical history were found, the care gap notification may identify gap information/data. In an example embodiment, gap information/data corresponding to an identified gap comprises information/data indicating the particular procedure, lab work, test, and/or the like that was not performed; the time window in which the particular procedure, lab work, test, and/or the like should have been performed in; and/or the like. In an example embodiment, the care gap notification comprises eligibility information/data corresponding to the patient/member.

The care gap module 226 may then provide the care gap notification. For example, the care gap module 226 may provide the care gap notification such that the provider computing entity and/or patient/member computing entity receives the care gap notification at step/operation 612. In various embodiments, the user computing entity 30 (e.g., provider or patient/member computing entity) that was being operated by the administrative and/or clinical staff corresponding to a provider or the patient/member to cause the care gap trigger indication to be generated may receive the care gap notification. In an example embodiment, the care gap notification may be provided to a patient/member computing entity corresponding to the patient/member (e.g., via SMS message, MMS message, instant message, email, an online portal, a dedicated application, and/or the like) and a provider computing entity corresponding to a provider associated with the patient/member (e.g., the provider the patient/member is scheduling an appointment with, a provider listed as a treating physician and/or primary doctor for the patient/member in a profile corresponding to the patient/member, and/or the like).

The provider computing entity and/or patient/member computing entity receives and processes the care gap notification. In an example embodiment, the processing of the care gap notification causes the provider computing entity and/or patient/member computing entity to provide a care gap evaluation 806. For example, FIG. 8 illustrates an example view of an appointment confirmation IUI 800. The appointment confirmation IUI 800 includes appointment information/data 802, an eligibility confirmation 804, and a care gap evaluation 806. In an example embodiment, the eligibility confirmation 804 and/or care gap evaluation 806 may provide at least a portion of the information/data provided in the care gap notification and/or a graphical representation thereof.

FIG. 7 illustrates an example data flow between a provider computing entity (e.g., an EMR and/or practice management system operating on the provider computing entity) and a mediator module 222, an eligibility module 224, and a care gap module 226 operating on a central computing entity 65 for providing a care gap evaluation. For example, the provider computing entity (e.g., as caused by the EMR and/or practice management system operating on the provider computing entity) provides (e.g., transmits) an authorization and/or authentication request 702 (e.g., comprising authorization, authentication, and/or credentialing information/data and/or other information/data identifying and/or confirming the identity of the provider). The mediator module 222 operating on the central computing entity 65 receives and analyzes the authorization and/or authentication request and provides an authentication and/or authorization response 704. For example, the authentication and/or authorization response 704 may include an authorization token (e.g., an Oauth token, in an example embodiment). The provider computing entity (e.g., as caused by the EMR and/or practice management system) receives the authentication and/or authorization response 704. The provider computing entity (e.g., as caused by the EMR and/or practice management system operating on the provider computing entity) may then provide (e.g., transmit) an eligibility authorization and/or authentication request 706 (e.g., comprising authorization and/or authentication information/data and/or the authorization token). The eligibility module 224 operating on the central computing entity 65 receives and analyzes the eligibility authorization and/or authentication request 706 and provides an eligibility authentication and/or authorization response 708. In an example embodiment, the eligibility module 224 links the authorization token to a particular transaction, set of authorization capabilities, and/or the like. In an example embodiment, the eligibility module 224 provides another token to the provider computing entity via the eligibility authentication and/or authorization response 708. The provider computing entity (e.g., as caused by the EMR and/or practice management system) receives the eligibility authentication and/or authorization response 708.

The provider computing entity (e.g., as caused by the EMR and/or practice management system operating thereon) may then provide (e.g., transmit) an eligibility request 710. In an example embodiment, the eligibility request 710 is encrypted using, for example, the authentication token. For example, the mediator module 222 may receive the eligibility request 710. In various embodiments, the eligibility request 710 includes patient/member identifying information/data, the authorization token, information/data identifying the provider, an indication of the appointment type and/or reason, and/or the like. In an example embodiment, the eligibility request 710 is a basic eligibility request. For example, the eligibility request 710 may be a request to ensure that the patient/member is an active member of a valid insurance plan. In various embodiments, the mediator module 222 may check the authorization token to ensure that the provider corresponding to the eligibility request 710 is authorized, authenticated, and/or appropriately credentialed to receive eligibility information/data responsive to the eligibility request 710. After and/or responsive to the mediator module 222 determines that the provider corresponding to the eligibility request 710 is authorized, authenticated, and/or appropriately credentialed to receive eligibility information/data responsive to the eligibility request 710, the mediator module 222 may reformat the eligibility request 710 and/or translate the eligibility request 710 to generate an eligibility inquiry 712. For example, the eligibility inquiry 712 may be an eligibility and/or benefits 270 inquiry. For example, various EMR and/or practice management systems may generate and provide eligibility requests having a variety of formats. The mediator module 222 may be configured and/or programmed to convert and/or translate the eligibility request 710 into a standardized eligibility inquiry 712 format. In an example embodiment, the eligibility inquiry 712 may be in JSON, SQL, and/or other data interchange format. The mediator module 222 may then provide the eligibility inquiry 712.

The eligibility module 224 may receive the eligibility inquiry 712. Responsive to receiving and/or reading the eligibility inquiry 712, the eligibility module 224 may use the patient/member identifying information/data to identify eligibility information/data corresponding to the identified patient/member in a patient/member data repository (e.g., file information/data 211, relational information/data 212, Hive information/data 213, data lake information information/data 214, a patient/member database, and/or the like). The eligibility module 224 may read the eligibility information/data from the patient/member data repository corresponding to the patient/member identified by the identifying information/data of the eligibility inquiry 712, and generate an eligibility response 714 based thereon. In various embodiments, generating the eligibility response 714 may comprise making one or more determinations based on the information/data provided in the eligibility inquiry 712 and eligibility information/data read from the patient/member data repository. For example, generating the eligibility response 714 may comprise analyzing information/data provided in the eligibility inquiry 712 based on the eligibility information/data read from the patient/member data repository. For example, the eligibility response 714 may comprise the identifying information/data identifying the patient/member, an indication of whether or not the patient/member is eligible for an appointment of the appointment type with the provider, a transaction identifier corresponding to the transaction of checking the patient/member eligibility, and/or the like. In various embodiments, the eligibility inquiry 712 is in JSON or another data interchange format. The eligibility module 224 may then provide the eligibility response 714. In an example embodiment, the eligibility response is an eligibility and/or benefits response 271.

The mediator module 222 may receive the eligibility response 714 and may convert and/or translate the eligibility response 714 into an eligibility confirmation 716. For example, in various embodiments, the mediator module 222 may convert and/or translate the eligibility request 714 into a format corresponding to the EMR and/or practice management system in communication with and/or being operated by the provider computing entity. For example, the eligibility request 710 may include an indication of the EMR and/or practice management system in communication with and/or being operated by the provider computing entity and the conversion and/or translation of the eligibility request 710 to the eligibility inquiry 712 and/or conversion and/or translation of the eligibility response 714 to the eligibility confirmation 716 may be based at least in part on the EMR and/or practice management system in communication with and/or operating on the provider computing entity. In an example embodiment, the eligibility confirmation 716 is encrypted. For example, the eligibility confirmation 716 may encrypted such that the authentication token is required for decrypting, reading, and/or extracting information from the eligibility confirmation 716.

The provider computing entity (e.g., as caused by the EMR and/or practice management system operating on the provider computing entity) may then provide (e.g., transmit) a care gap authorization and/or authentication request 718 (e.g., comprising authorization and/or authentication information/data and/or the authorization token). The care gap module 226 operating on the central computing entity 65 receives and analyzes the care gap authorization and/or authentication request 718 and provides a care gap authentication and/or authorization response 720. In an example embodiment, the care gap module 226 links the authorization token to a particular transaction, set of authorization capabilities, and/or the like. In an example embodiment, the care gap module 226 provides another token to the provider computing entity via the care gap authentication and/or authorization response 720. The provider computing entity (e.g., as caused by the EMR and/or practice management system) receives the care gap authentication and/or authorization response 720.

The provider computing entity (e.g., as caused by the EMR and/or practice management system operating thereon) may then provide (e.g., transmit) a care gap request 722. In an example embodiment, the care gap request 722 is encrypted using, for example, the authentication token. For example, the provider computing entity may encrypt and then provide the care gap request 722. For example, the mediator module 222 may receive the care gap request 722. In various embodiments, the care gap request 722 comprises the trigger indication, information/data that causes and/or triggers the listener 220 to generate the trigger indication, and/or information/data that may be used to generate a trigger indication. In various embodiments, the mediator module 222 may check the authorization token to ensure that the provider corresponding to the care gap request 722 is authorized, authenticated, and/or appropriately credentialed to receive a care gap notification responsive to the care gap request 722. After and/or responsive to the mediator module 222 determining that the provider corresponding to the care gap request 722 is authorized, authenticated, and/or appropriately credentialed to receive a care gap notification responsive to the care gap request 722, the mediator module 222 may reformat the care gap request 722 and/or translate the care gap request 722 to generate a care gap inquiry 724. For example, the care gap inquiry 722 may be and/or comprise the trigger indication. For example, various EMR and/or practice management systems may generate and provide care gap requests having a variety of formats. The mediator module 222 may be configured and/or programmed to convert and/or translate the care gap request 722 into a standardized care gap inquiry 724 and/or trigger indication format. The mediator module 222 may then provide the care inquiry 724.

The care gap module 226 may receive the care gap inquiry 724. Responsive to receiving and/or reading the care gap inquiry 724 (e.g., receiving and/or reading the trigger indication), the care gap module 226 may generate and provide an extended eligibility request 726. The eligibility module 724 may receive the extended eligibility request 726, perform the extended eligibility check (e.g., based on patient/member identifying information/data provided in the extended eligibility request 726), and provide an extended eligibility response 728. For example, the extended eligibility request 726 may include a request for eligibility information/data corresponding to particular procedures, lab work, tests, and/or the like. The eligibility module 224 may determine the eligibility information/data provided in the extended eligibility response 728 based on details of the insurance plan of which the patient/member is an active member, one or more accumulators associated with the patient/member, and/or the like.

The care gap module 226 may then receive the extended eligibility response 726. The care gap module 226 may perform the care gap check. In an example embodiment, the care gap check is performed based at least in part on the eligibility information/data received in the extended eligibility response 728. In an example embodiment, the extended eligibility request 726 is generated and provided after performing the care gap check and/or while the care gap check is in process. For example, as described above, the care gap module 226 may identify one or more care standards that are relevant and/or applicable to the patient/member (e.g., based on the demographics of the patient/member, the medical history of the patient/member, and/or eligibility information/data). The care gap module 226 may then determine if any gaps in care are present based on the identified one or more relevant and/or applicable care standards and the patient/member's medical history. The care gap module 226 may then generate and provide a care gap response 730 comprising an indication of whether or not any care gaps for the patient/member were identified, information/data identifying any care gaps that were found/identified, frequency information/data for any found/identified care gaps, eligibility information/data, and/or the like.

The mediator module 222 may receive the care gap response 730 and may convert and/or translate the care gap response 730 into a care gap notification 732. For example, in various embodiments, the mediator module 222 may convert and/or translate the care gap response 732 into a format corresponding to the EMR and/or practice management system in communication with and/or being operated by the provider computing entity. For example, the care gap request 722 may include an indication of the EMR and/or practice management system in communication with and/or being operated by the provider computing entity and the conversion and/or translation of the care gap request 722 to the care gap inquiry 724 and/or conversion and/or translation of the care gap response 730 to the care gap notification 732 may be based at least in part on the EMR and/or practice management system in communication with and/or operating on the provider computing entity. In an example embodiment, the care gap notification 732 is encrypted. For example, the central computing entity 65 may encrypt the care gap notification 732 such that the authentication token is required for decrypting, reading, and/or extracting information from the care gap notification 732.

The provider computing entity may receive, read, and/or analyze the care gap notification and provide and/or display a care gap evaluation 806 and/or an eligibility confirmation 804. For example, the care gap evaluation 806 may be provided and/or displayed via an appointment confirmation IUI 800 or other IUI corresponding to the EMR and/or practice management system operated by and/or on behalf of the provider.

b. Exemplary Care Estimate Evaluation

In various embodiments, a care estimate evaluation may be provided via an IUI corresponding to an EMR and/or practice management system operated by and/or on behalf of the provider. A care estimate evaluation may be provided and/or displayed via an output device/interface of a user computing entity 30 (e.g., provider computing entity and/or patient/member computing entity). In various embodiments, a care estimate evaluation comprises a cost estimate for one or more procedures, lab work, tests, services and/or the like (referred to collectively as services herein). In an example embodiment, the cost estimate is determined based on the insurance information/data of the patient/member. In an example embodiment, the cost estimate is an out-of-pocket cost estimate for the patient/member. In an example embodiment, the cost estimate evaluation may identify one or more providers that is credentialed for performing the one or more services and the cost estimate provided is specific to the corresponding provider (e.g., the cost that provider would charge the patient/member for that service and/or that the patient/member would need to pay out of pocket to have that provider perform that service).

For example, FIG. 9 illustrates an example care estimate evaluation IUI 900. The care estimate evaluation IUI 900 includes patient/member identifying information/data 902 identifying the patient/member that the care estimate evaluation corresponds to and one or more services evaluations 910. Each service evaluation 910 corresponds to a particular service (e.g., LAB1234, LAB5678). One or more providers are identified for each particular service. For example, a service evaluation 910 may comprise provider identifying information/data 912 such as a provider name, a provider location, distance to the provider's location from the patient/member's home, office, and/or the like. In an example embodiment, a service evaluation 910 includes a cost estimate 916 for each identified provider. In an example embodiment, a care estimate evaluation IUI 900 provides a patient/member or administrative and/or clinical staff with the ability to schedule one or more services. For example, for one or more service evaluations 910, an operator of a user computing entity 30 (e.g., provider computing entity or patient/member computing entity) may use selectors 914 to select a provider for a service and initiate scheduling of the service with the provider (e.g., by selecting the schedule now selectable element 904). In various embodiments, the care estimate evaluation IUI 900 may include a schedule later selectable element 906 for scheduling the performance of the one or more services at a later time.

In various embodiments, a care estimate evaluation may be provided in response to a patient/member or administrative and/or clinical staff selecting a provide care estimate selectable element 808 that may be provided with a care gap evaluation (e.g., to have a care estimate for services corresponding to any identified gaps in care for the patient/member) and/or other service ordering or referring IUI of the EMR and/or practice management system. For example, a lab ordering IUI, prescription prescribing IUI, referral IUI and/or the like of the EMR and/or practice management system may include a provide care estimate selectable element 808. For example, FIG. 10 illustrates an example patient chart view IUI 1000 of an IUI provided by an EMR and/or practice management system. In various embodiments, the patient chart view IUI 1000 may be provided via a provider computing entity. For example, the patient chart view IUI 1000 may include a patient identifying section 1002 providing patient identifying information/data (e.g., patient name, preferred name, sex, date of birth, social security number, age, a patient identifier, insurance plan name, insurance plan member number, and/or the like), patient contact information/data section 1004 (e.g., mailing address, phone number(s), email address, and/or the like), current medications section 1006, care gap evaluation 1008, and medical history section 1010. In an example embodiment, the medical history section 1010 comprises a diagnoses/conditions section 1012 listing various conditions with which the patient/member has been diagnosed, and a procedures section 1014 listing various procedures, lab work, tests, and/or other services that the been performed for the patient/member. In various embodiments, the patient care view IUI 1000 may include on or more selectable elements 1018 that an administrative or clinical staff may interact with (e.g., click, select, and/or the like via a user input device/interface of a provider computing entity) to add and/or update the patient/member's EMR, view additional portions of the patient/member's EMR, and/or the like. In various embodiments, the patient chart view IUI 1000 may include a care estimate selectable element 1016. In various embodiments, when administrative and/or clinical staff of the provider interacts with (e.g., selects, clicks and/or the like via a user input device/interface of the provider computing entity) the care estimate selectable element 1016 to trigger the EMR and/or practice management system to provide a care estimate request IUI 1100, an example of which is shown in FIG. 11.

In various embodiments, administrative and/or clinical staff of provider may enter and/or select (e.g., via a user input device/interface of a provider computing entity) information/data into one or more data fields of a care estimate request IUI 1100 for requesting a care estimate. For example, administrative and/or clinical staff may select and/or enter patient/member identifying information in the patient/member identifying section 1102 of the care estimate request IUI 1100 to identify the patient/member for whom the care estimate evaluation is to be provided. For example, administrative and/or clinical staff may select and/or enter service identifying information in the service section 1104 of the care estimate request IUI 1100 to identify one or more services for which care estimates are requested for the patient/member. For example, administrative and/or clinical staff may select and/or enter facility information in the facility section 1106 of the care estimate request IUI 1100 to identify a particular facility and/or configurable distance within which appropriate facilities and/or potential providers may be searched for providing the care estimate evaluation for the patient/member. The administrative and/or clinical staff may then interact with the run care estimate selectable element 1108 to cause the EMR and/or practice management system (e.g., operating on the provider computing entity) to trigger and/or cause the triggering of care estimate back-end functionality of the central computing entity 65.

In another example embodiment, a listener 220 operating on a central computing entity 65 and/or provider computing entity may determine that administrative and/or clinical staff of a provider has provided user input via an IUI of the EMR and/or practice management system ordering lab work, prescribing a prescription, indicating a referral, and/or the like and may initiate the generation and providing of a care estimate evaluation. In an example embodiment, the generation and providing of a care estimate evaluation may be triggered by administrative and/or clinical staff operating a provider computing entity and the care estimate evaluation may be provided to a patient/member computing entity. For example, administrative and/or clinical staff may enter information/data via an IUI (e.g., a patient cart view IUI 1000) of the EMR and/or practice management system that the patient/member is recommend to receive a particular service. The listener 220 may identify that a service has been recommended for a patient/member and may cause the triggering of care estimate back-end functionality of the central computing entity 65. In various embodiments one or more providers are identified during the generation of the care estimate evaluation. For example, the central computing entity 65 may store (e.g., in memory media 206) and/or be able to access a map data repository comprising map information/data and/or a provider data repository provider information/data corresponding to a plurality of providers. For example, the provider information/data corresponding to a provider comprises a provider name, provider credentials, provider location (e.g., street and/or mailing address of provider's office), provider contact information (e.g., phone number, email, URL for accessing an online portal operated by and/or on behalf of the provider), provider practice area/specialties, provider standing with one or more insurance companies and/or plans, and/or the like. In an example embodiment, the provider information/data corresponding to the provider comprises one or more fee schedules for one or more services provided by the provider. For example, if the provider is an imaging center, the fee schedule may include fees for various imaging services offered by the provider. If the provider is a lab, the fee schedule may include fees for various lab work that may be performed by the provider. If the provider is a pharmacy, the fee schedule may include fees for various prescriptions and/or pharmaceuticals offered for sale by the pharmacy. In an example embodiment, the fee schedule reflects fees negotiated between the provider and an insurance company. For example, fee schedule may reflect out of pocket costs for a patient/member that is an active member of a particular insurance pan.

FIG. 12 provides a flowchart illustrating various processes, procedures, and/or the like that may be performed by a central computing entity 65 to generate and provide a care estimate evaluation. For example, a patient/member may operate a patient/member computing entity (which is an example of a user computing entity 30) and/or administrative and/or clinical staff associated with a provider may operate a provider computing entity (which is another example of a user computing entity 30) to interact with an IUI associated with an EMR and/or practice management system operated by and/or on behalf of the provider and/or to otherwise provide input to the EMR and/or practice management system. For example, the patient/member and/or administrative and/or clinical staff may provide user input (e.g., via a user input device/interface of a user computing entity 30) to check for gaps in care for a patient/member; order labs or test for the patient/member; prescribe a prescription to the patient/member; enter a referral and/or a treatment plan for a patient/member; add and/or update information/data of the patient/member's EMR (e.g., to add symptoms reported by patient, lab or other test results, codes based on provider notes and/or determinations, etc.); release/discharge the patient/member from a clinic, hospital, or other facility; select a care estimate selectable element 808 of the IUI; and/or the like. In response to receiving the user input, the EMR and/or practice management system (e.g., operating on the provider computing entity) and/or a listener 220 (e.g., operating on the central computing entity 65 and/or the provider computing entity) may generate a care estimate trigger indication. The care estimate trigger indication may then be provided (e.g., by the listener 220 and/or the EMR and/or practice management system) such that the mediator module 222 receives the care estimate trigger indication.

At step/operation 1202, the care estimate trigger indication is received. For example, the mediator module 222 operating on the central computing entity 65 may receive the care estimate trigger indication. In various embodiments, the care estimate trigger indication comprises trigger information/data. In various embodiments, the trigger information/data includes identifying information/data identifying the corresponding patient/member (e.g., patient identifier configured to uniquely identify the patient/member, patient/member name, patient/member birth date, patient/member address, and/or the like), a patient location (e.g., home address, office address, and/or the like), patient/member insurance policy information/data (e.g., plan number, group number, and/or the like), trigger cause information/data (e.g., what caused the trigger indication to be generated—patient scheduling an appointment and reporting particular symptoms; a referral/care plan for the patient/member being entered; labs or test being ordered; a prescription being prescribed; information/data of the patient/member's EMR being added to and/or updated; and/or the like), current medical information/data for the patient/member (e.g., current symptoms, in text or standardized medical codes), historical medical information/data for the patient/member (e.g., medical information/data stored in the EMR corresponding to the patient/member), an indication that a care estimate has been triggered, a type and/or version of the EMR and/or practice management system corresponding to and/or being operated by the provider computing entity, authentication and/or authorization information/data for the provider, and/or the like.

At step/operation 1204, at least some of the trigger information/data is extracted from the care estimate trigger indication. For example, the mediator module 222 (and/or the care estimate module 230) operating on the central computing entity 65 may extract at least some of the trigger information/data from the care estimate trigger indication. The care estimate module 230 may receive the extracted trigger information/data and determine if any other information/data is needed for identifying one or more services that estimates are to be provided for, one or more providers that can provide the services, determining estimates for the services, and/or the like. At step 1206, the care estimate module 230 may request and receive any additional information/data (e.g., in addition to the information/data extracted from the care estimate trigger indication). For example, the care estimate module 230 may issue one or more API calls to access information/data stored by the EMR and/or practice management system and/or in a patient/member data repository and/or a provider data repository. In an example embodiment, the care estimate module 230 may determine which API calls to issue based at least in part on the type and/or version of the EMR and/or practice management system corresponding to and/or being operated by the provider computing entity extracted from the care gap trigger indication. For example, the API calls issued may be for one or more APIs exposed by and/or associated with the on the type and/or version of the EMR and/or practice management system indicated by the care gap trigger indication.

At step/operation 1208, eligibility information/data may be requested and received. For example, the care estimate module 230 may request eligibility information/data for the patient/member from the eligibility module 224. For example, the care estimate module 230 may generate and provide an eligibility check request comprising identifying information/data for the patient/member. For example, the eligibility check may include checking to confirm that the patient/member is an active member of an insurance plan and/or to determine which insurance plan the patient/member is an active member of. The eligibility module 224 may receive the eligibility check request, access eligibility information/data corresponding to the patient/member, and provide the eligibility information/data. The care estimate module 230 may then receive the eligibility information/data.

At step/operation 1210, map information/data may be accessed from the map data repository and provider information/data may be accessed from the provider data repository. For example, the care estimate module 230 may access map information/data and provider information/data. The care estimate module 230 may then use the map information/data and provider information/data to identify one or more potential providers that can provide a service indicated by the care estimate trigger indication (and/or information/data requested and received by the care estimate module 230 at step/operation 1006) within a distance threshold of the patient location. In various embodiments, the distance threshold is a predetermined distance (e.g., 20 miles, 10 miles, 5 miles, 2 miles, and/or the like) or a user provided distance (e.g., stored in the patient/member information/data and/or provided via the IUI). In an example embodiment, when more than a threshold number (e.g., two, five, eight, and/or the like) of potential providers are identified for a service, the provider standing with the insurance company and/or plan that the patient/member is an active member of, may be used to filter the potential providers down to the threshold number.

At step/operation 1212, estimates for the one or more services corresponding to the care estimate trigger indication are determined for each of the potential providers. For example, the care estimate module 230 may determine estimates for the one or more services corresponding to the care estimate trigger indication for each of the one or more services for each of the potential providers. For example, the care estimate module 230 may use a fee schedule corresponding to a potential provider to determine an estimate for a service to be provided by the potential provider. In an example embodiment, the central computing entity 65 may provide (e.g., transmit) an estimate request (possibly via an API call) to a user computing entity 30 operated by and/or on behalf of a potential provider and receive an estimate response in response to the estimate request. The estimate response may include an estimated fee for provision of a service by the provider for the patient/member based on the patient/member's insurance plan.

The care estimate module 230 may then generate a care estimate notification. In various embodiments, the care estimate notification comprises one or more potential provider names, locations, and cost estimates for each service identified in the care estimate trigger indication (and/or accessed/retrieved at step/operation 1206). In an example embodiment, the care estimate notification comprises eligibility information/data corresponding to the patient/member.

The care estimate module 230 may then provide the care estimate notification at step/operation 1214. For example, the care estimate module 230 may provide the care estimate notification such that the provider computing entity and/or patient/member computing entity receives the care estimate notification. In various embodiments, the user computing entity 30 (e.g., provider or patient/member computing entity) that was being operated by the administrative and/or clinical staff corresponding to a provider or the patient/member to cause the care estimate trigger indication to be generated may receive the care estimate notification. In an example embodiment, a patient/member computing entity corresponding to the patient/member identified in the care estimate trigger indication may receive the care estimate notification. In an example embodiment, the care estimate notification may be provided to a patient/member computing entity corresponding to the patient/member (e.g., via SMS message, MMS message, instant message, email, an online portal, a dedicated application, and/or the like) and/or a provider computing entity corresponding to a provider associated with the patient/member (e.g., the provider the that entered the care/plan/referral/lab work order/prescription, a provider listed as a treating physician and/or primary doctor for the patient/member in a profile corresponding to the patient/member, and/or the like).

The provider computing entity and/or patient/member computing entity receives and processes the care estimate notification. In an example embodiment, the processing of the care estimate notification causes the provider computing entity and/or patient/member computing entity to provide a care estimate evaluation 900. For example, the care estimate evaluation IUI 900 may include one or more service evaluations 910, with service evaluation 910 corresponding to a particular service. For example, a service evaluation 910 may comprise provider identifying information/data 912 such as a provider name, a provider location, distance of the provider's location from the patient/member's home, office, and/or the like. In an example embodiment, a service evaluation 910 includes the determined cost estimate 916 for each identified potential provider. In an example embodiment, a care estimate evaluation IUI 900 provides a patient/member or administrative and/or clinical staff with the ability to schedule one or more services. For example, for one or more service evaluations 910, an operator of a user computing entity 30 (e.g., provider computing entity or patient/member computing entity) may use selectors 914 to select a provider for a service and initiate scheduling of the service with the provider (e.g., by selecting the schedule now selectable element 904).

FIG. 13 illustrates an example data flow between a provider computing entity (e.g., an EMR and/or practice management system operating on the provider computing entity) and a mediator module 222, an eligibility module 224, an authorization module 228, and a care estimate module 230 operating on a central computing entity 65 for providing a care estimate evaluation. For example, the provider computing entity (e.g., as caused by the EMR and/or practice management system operating on the provider computing entity) provides (e.g., transmits) an authorization and/or authentication request 1302 (e.g., comprising authorization, authentication, and/or credentialing information/data and/or other information/data identifying and/or confirming the identity of the provider). The mediator module 222 operating on the central computing entity 65 receives and analyzes the authorization and/or authentication request and provides an authentication and/or authorization response 1304. For example, the authentication and/or authorization response 1304 may include an authorization token (e.g., an Oauth token, in an example embodiment). The provider computing entity (e.g., as caused by the EMR and/or practice management system) receives the authentication and/or authorization response 1304. The provider computing entity (e.g., as caused by the EMR and/or practice management system operating on the provider computing entity) may then provide (e.g., transmit) an eligibility authorization and/or authentication request 1306 (e.g., comprising authorization and/or authentication information/data and/or the authorization token). The eligibility module 224 operating on the central computing entity 65 receives and analyzes the eligibility authorization and/or authentication request 1306 and provides an eligibility authentication and/or authorization response 1308. In an example embodiment, the eligibility module 224 links the authorization token to a particular transaction, set of authorization capabilities, and/or the like. In an example embodiment, the eligibility module 224 provides another token to the provider computing entity via the eligibility authentication and/or authorization response 1308. The provider computing entity (e.g., as caused by the EMR and/or practice management system) receives the eligibility authentication and/or authorization response 1308.

The provider computing entity (e.g., as caused by the EMR and/or practice management system operating thereon) may then provide (e.g., transmit) an eligibility request 1310. For example, the mediator module 222 may receive the eligibility request 1310. In an example embodiment, the eligibility request 1310 may be encrypted using the authentication token. In various embodiments, the eligibility request 1310 includes patient/member identifying information/data, the authorization token, information/data identifying the provider, an indication of the appointment type and/or reason, and/or the like. In an example embodiment, the eligibility request 1310 is a basic eligibility request. For example, the eligibility request 1310 may be a request to ensure that the patient/member is an active member of a valid insurance plan. In various embodiments, the mediator module 222 may check the authorization token to ensure that the provider corresponding to the eligibility request 1310 is authorized, authenticated, and/or appropriately credentialed to receive eligibility information/data responsive to the eligibility request 1310. After and/or responsive to the mediator module 222 determines that the provider corresponding to the eligibility request 1310 is authorized, authenticated, and/or appropriately credentialed to receive eligibility information/data responsive to the eligibility request 1310, the mediator module 222 may reformat the eligibility request 1310 and/or translate the eligibility request 1310 to generate an eligibility inquiry 1312. For example, the eligibility inquiry 1312 may be an eligibility and/or benefits 270 inquiry. For example, various EMR and/or practice management systems may generate and provide eligibility requests having a variety of formats. The mediator module 222 may be configured and/or programmed to convert and/or translate the eligibility request 1310 into a standardized eligibility inquiry 1312 format. In an example embodiment, the eligibility inquiry 1312 may be in JSON, SQL, and/or other data interchange format. The mediator module 222 may then provide the eligibility inquiry 1312.

The eligibility module 224 may receive the eligibility inquiry 1312. Responsive to receiving and/or reading the eligibility inquiry 1312, the eligibility module 224 may use the patient/member identifying information/data to identify eligibility information/data corresponding to the identified patient/member in a patient/member data repository (e.g., file information/data 211, relational information/data 212, Hive information/data 213, data lake information information/data 214, a patient/member database, and/or the like). The eligibility module 224 may read the eligibility information/data from the patient/member data repository corresponding to the patient/member identified by the identifying information/data of the eligibility inquiry 1312, and generate an eligibility response 1314 based thereon. In various embodiments, generating the eligibility response 1314 may comprise making one or more determinations based on the information/data provided in the eligibility inquiry 1312 and eligibility information/data read from the patient/member data repository. For example, generating the eligibility response 1314 may comprise analyzing information/data provided in the eligibility inquiry 1312 based on the eligibility information/data read from the patient/member data repository. For example, the eligibility response 1314 may comprise the identifying information/data identifying the patient/member, an indication of whether or not the patient/member is eligible for an appointment of the appointment type with the provider, a transaction identifier corresponding to the transaction of checking the patient/member eligibility, and/or the like. In various embodiments, the eligibility inquiry 1312 is in JSON or another data interchange format. The eligibility module 224 may then provide the eligibility response 1314. In an example embodiment, the eligibility response is an eligibility and/or benefits response 271.

The mediator module 222 may receive the eligibility response 1314 and may convert and/or translate the eligibility response 1314 into an eligibility confirmation 1316. For example, in various embodiments, the mediator module 222 may convert and/or translate the eligibility request 1314 into an eligibility confirmation 1316 in a format corresponding to the EMR and/or practice management system in communication with and/or being operated by the provider computing entity. In an example embodiment, the eligibility confirmation 1316 is encrypted. For example, the eligibility confirmation 1316 may be encrypted such that the authentication token is required for decrypting, reading, and/or extracting information/data from the eligibility confirmation 1316. For example, the eligibility request 1310 may include an indication of the EMR and/or practice management system in communication with and/or being operated by the provider computing entity and the conversion and/or translation of the eligibility request 1310 to the eligibility inquiry 1312 and/or conversion and/or translation of the eligibility response 1314 to the eligibility confirmation 1316 may be based at least in part on the EMR and/or practice management system in communication with and/or operating on the provider computing entity.

The provider computing entity (e.g., as caused by the EMR and/or practice management system operating on the provider computing entity) may then provide (e.g., transmit) a care estimate authorization and/or authentication request 1318 (e.g., comprising authorization and/or authentication information/data and/or the authorization token). The care estimate module 230 operating on the central computing entity 65 receives and analyzes the care estimate authorization and/or authentication request 1318 and provides a care estimate authentication and/or authorization response 1320. In an example embodiment, the care estimate module 230 links the authorization token to a particular transaction, set of authorization capabilities, and/or the like. In an example embodiment, the care estimate module 230 provides another token to the provider computing entity via the care estimate authentication and/or authorization response 1320. The provider computing entity (e.g., as caused by the EMR and/or practice management system) receives the care estimate authentication and/or authorization response 1320.

The provider computing entity (e.g., as caused by the EMR and/or practice management system operating thereon) may then provide (e.g., transmit) a care estimate request 1322. For example, the mediator module 222 may receive the care estimate request 1322. In an example embodiment, the care estimate request 1322 is encrypted using, for example, the authentication token. In various embodiments, the care estimate request 1322 comprises the trigger indication, information/data that causes and/or triggers the listener 220 to generate the trigger indication, and/or information/data that may be used to generate a trigger indication. In various embodiments, the mediator module 222 may check the authorization token to ensure that the provider corresponding to the care estimate request 1322 is authorized, authenticated, and/or appropriately credentialed to receive a care estimate notification responsive to the care estimate request 1322. After and/or responsive to the mediator module 222 determining that the provider corresponding to the care estimate request 1322 is authorized, authenticated, and/or appropriately credentialed to receive a care estimate notification responsive to the care estimate request 1322, the mediator module 222 may reformat the care estimate request 1322 and/or translate the care estimate request 1322 to generate a care estimate inquiry 1324. For example, the care estimate inquiry 1322 may be and/or comprise the care estimate trigger indication. For example, various EMR and/or practice management systems may generate and provide care estimate requests having a variety of formats. The mediator module 222 may be configured and/or programmed to convert and/or translate the care estimate request 1322 into a standardized care estimate inquiry 1324 and/or trigger indication format. The mediator module 222 may then provide the care estimate inquiry 1324.

The care estimate module 230 may receive the care estimate inquiry 1324. Responsive to receiving and/or reading the care estimate inquiry 1324 (e.g., receiving and/or reading the trigger indication), the care estimate module 230 may generate and provide an extended eligibility request 1326. The eligibility module 224 may receive the extended eligibility request 1326, perform the extended eligibility check (e.g., based on patient/member identifying information/data provided in the extended eligibility request 1326), and provide an extended eligibility response 1332. For example, the extended eligibility request 1326 may include a request for eligibility information/data corresponding to particular services, providers, and/or the like. The eligibility module 224 may determine the eligibility information/data provided in the extended eligibility response 1332 based on details of the insurance plan of which the patient/member is an active member, one or more accumulators associated with the patient/member, and/or the like. The care estimate module 230 may then receive the extended eligibility response 1332.

The care estimate module 230 may generate and provide an authorization request 1328. For example, the care estimate module 230 may determine if one or more of the services indicated in the trigger indication require prior authorization. If prior authorization for a service is required, the care estimate module 230 may generate a corresponding authorization request 1328 and provide the authorization request 1328 such that an authorization module 228 receives the authorization request 1328. The authorization module 228 may be configured and/or programmed to perform prior authorization functions. For example, the authorization module 228 may determine if the patient/member (e.g., based on the patient/member insurance plan) is authorized to receive a particular service and provide a prior authorization for the service. The authorization module 228 may then generate and provide an authorization response 1330. The authorization response 1330 may include an indication that the patient/member has been pre-authorized to have the service performed. In an example embodiment, the authorization response 1330 may include prior authorization information/data indicating that the patient/member has been pre-authorized to have the service performed by one or more potential providers identified during the care estimate (e.g., at step/operation 1210 as described above). The care estimate module 230 may receive the authorization request 1330.

The care estimate module 230 may perform the care estimate and generate the care estimate notification. In an example embodiment, the care estimate is performed based at least in part on the eligibility information/data received in the extended eligibility response 1332 and/or the authorization response 1330. In an example embodiment, the extended eligibility request 1326 and/or authorization request 1328 is generated and provided after performing the care estimate (e.g., after identifying the one or more potential providers for each service) and/or while the care estimate is in process. For example, as described above, the care estimate module 230 may identify one or more potential providers within a predefined and/or user-configurable distance threshold for each service indicated in the trigger indication (e.g., included in the care estimate inquiry 1324). The care estimate module 230 may then determine cost estimates for each potential provider for each service. The care estimate module 230 may then generate and provide a care estimate response 1334 comprising the potential providers identified for each service and corresponding provider information/data (e.g., provider name, provider location, provider contact information/data) and corresponding cost estimates for the potential provider to provide the service, eligibility information/data, prior authorization information/data, and/or the like.

The mediator module 222 may receive the care estimate response 1334 and may convert and/or translate the care estimate response 1334 into a care estimate notification 1336. For example, in various embodiments, the mediator module 222 may convert and/or translate the care estimate response 1334 into a format corresponding to the EMR and/or practice management system in communication with and/or being operated by the provider computing entity. For example, the care estimate request 1322 may include an indication of the EMR and/or practice management system in communication with and/or being operated by the provider computing entity and the conversion and/or translation of the care estimate request 1322 to the care estimate inquiry 1324 and/or conversion and/or translation of the care estimate response 1334 to the care estimate notification 1336 may be based at least in part on the EMR and/or practice management system in communication with and/or operating on the provider computing entity. In an example embodiment, the care estimate notification 1336 may be encrypted. For example, the care estimate notification 1336 may be encrypted such that the authentication token is required for decrypting, reading, and/or extracting information from the care estimate notification 1336.

The provider computing entity and/or patient/member computing entity may receive, read, and/or analyze the care estimate notification and provide and/or display a care estimate evaluation IUI 900 corresponding to the EMR and/or practice management system operated by and/or on behalf of the provider.

FIG. 14 illustrates an example data flow between a provider computing entity (e.g., an EMR and/or practice management system operating on the provider computing entity) and a mediator module 222, an eligibility module 224, an authorization module 228, a care estimate module 230, and lab module 232 or RX module 234 operating on a central computing entity 65 for providing a care estimate evaluation responsive to a provider ordering lab work and/or entering a prescription for a patient/member via user input (e.g., by administrative and/or clinical staff of the provider) via an IUI of the EMR and/or practice management system. For example, a lab module 232 may be configured to interface with computing entities of one or more providers who provide lab work services. In an example embodiment, an RX module 234 may be configured to interface with computing entities of one or more pharmacies. For example, the data flow shown in FIG. 14 may illustrate how a care estimate evaluation is provided in a scenario where the service(s) corresponding to the care estimate evaluation are lab work and/or prescriptions.

In an example embodiment, the provider computing entity (e.g., as caused by the EMR and/or practice management system operating on the provider computing entity) provides (e.g., transmits) an authorization and/or authentication request 1402 (e.g., comprising authorization, authentication, and/or credentialing information/data and/or other information/data identifying and/or confirming the identity of the provider). The mediator module 222 operating on the central computing entity 65 receives and analyzes the authorization and/or authentication request and provides an authentication and/or authorization response 1404. For example, the authentication and/or authorization response 1404 may include an authorization token (e.g., an Oauth token, in an example embodiment). The provider computing entity (e.g., as caused by the EMR and/or practice management system) receives the authentication and/or authorization response 1404. The provider computing entity (e.g., as caused by the EMR and/or practice management system operating on the provider computing entity) may then provide (e.g., transmit) an eligibility authorization and/or authentication request 1406 (e.g., comprising authorization and/or authentication information/data and/or the authorization token). The eligibility module 224 operating on the central computing entity 65 receives and analyzes the eligibility authorization and/or authentication request 1406 and provides an eligibility authentication and/or authorization response 1408. In an example embodiment, the eligibility module 224 links the authorization token to a particular transaction, set of authorization capabilities, and/or the like. In an example embodiment, the eligibility module 224 provides another token to the provider computing entity via the eligibility authentication and/or authorization response 1408. The provider computing entity (e.g., as caused by the EMR and/or practice management system) receives the eligibility authentication and/or authorization response 1408.

The provider computing entity (e.g., as caused by the EMR and/or practice management system operating thereon) may then provide (e.g., transmit) an eligibility request 1410. In an example embodiment, the eligibility request 1410 is encrypted using, for example, the authentication token. For example, the mediator module 222 may receive the eligibility request 1410. In various embodiments, the eligibility request 1410 includes patient/member identifying information/data, the authorization token, information/data identifying the provider, an indication of the appointment type and/or reason, and/or the like. In an example embodiment, the eligibility request 1410 is a basic eligibility request. For example, the eligibility request 1410 may be a request to ensure that the patient/member is an active member of a valid insurance plan. In various embodiments, the mediator module 222 may check the authorization token to ensure that the provider corresponding to the eligibility request 1410 is authorized, authenticated, and/or appropriately credentialed to receive eligibility information/data responsive to the eligibility request 1410. After and/or responsive to the mediator module 222 determines that the provider corresponding to the eligibility request 1410 is authorized, authenticated, and/or appropriately credentialed to receive eligibility information/data responsive to the eligibility request 1410, the mediator module 222 may reformat the eligibility request 1410 and/or translate the eligibility request 1410 to generate an eligibility inquiry 1412. For example, the eligibility inquiry 1412 may be an eligibility and/or benefits 270 inquiry. For example, various EMR and/or practice management systems may generate and provide eligibility requests having a variety of formats. The mediator module 222 may be configured and/or programmed to convert and/or translate the eligibility request 1410 into a standardized eligibility inquiry 1412 format. In an example embodiment, the eligibility inquiry 1412 may be in JSON, SQL, and/or other data interchange format. The mediator module 222 may then provide the eligibility inquiry 1412.

The eligibility module 224 may receive the eligibility inquiry 1412. Responsive to receiving and/or reading the eligibility inquiry 1412, the eligibility module 224 may use the patient/member identifying information/data to identify eligibility information/data corresponding to the identified patient/member in a patient/member data repository (e.g., file information/data 211, relational information/data 212, Hive information/data 213, data lake information information/data 214, a patient/member database, and/or the like). The eligibility module 224 may read the eligibility information/data from the patient/member data repository corresponding to the patient/member identified by the identifying information/data of the eligibility inquiry 1412, and generate an eligibility response 1414 based thereon. In various embodiments, generating the eligibility response 1414 may comprise making one or more determinations based on the information/data provided in the eligibility inquiry 1412 and eligibility information/data read from the patient/member data repository. For example, generating the eligibility response 1414 may comprise analyzing information/data provided in the eligibility inquiry 1412 based on the eligibility information/data read from the patient/member data repository. For example, the eligibility response 1414 may comprise the identifying information/data identifying the patient/member, an indication of whether or not the patient/member is eligible for an appointment of the appointment type with the provider, a transaction identifier corresponding to the transaction of checking the patient/member eligibility, and/or the like. In various embodiments, the eligibility inquiry 1412 is in JSON or another data interchange format. The eligibility module 224 may then provide the eligibility response 1414. In an example embodiment, the eligibility response is an eligibility and/or benefits response 271.

The mediator module 222 may receive the eligibility response 1414 and may convert and/or translate the eligibility response 1414 into an eligibility confirmation 1416. For example, in various embodiments, the mediator module 222 may convert and/or translate the eligibility request 1414 into a format corresponding to the EMR and/or practice management system in communication with and/or being operated by the provider computing entity. For example, the eligibility request 1410 may include an indication of the EMR and/or practice management system in communication with and/or being operated by the provider computing entity and the conversion and/or translation of the eligibility request 1410 to the eligibility inquiry 1412 and/or conversion and/or translation of the eligibility response 1414 to the eligibility confirmation 1416 may be based at least in part on the EMR and/or practice management system in communication with and/or operating on the provider computing entity. In an example embodiment, the eligibility confirmation 1416 is encrypted such that the authentication token is required for decrypting, reading, and/or extracting information from the eligibility confirmation 1416.

The provider computing entity (e.g., as caused by the EMR and/or practice management system operating on the provider computing entity) may then provide (e.g., transmit) a prior authorization (PA) authorization and/or authentication request 1418 (e.g., comprising authorization and/or authentication information/data and/or the authorization token). The authorization module 228 operating on the central computing entity 65 receives and analyzes the PA authorization and/or authentication request 1418 and provides a PA authentication and/or authorization response 1420. In an example embodiment, the authorization module 228 links the authorization token to a particular transaction, set of authorization capabilities, and/or the like. In an example embodiment, the authorization module 228 provides another token to the provider computing entity via the PA authentication and/or authorization response 1420. The provider computing entity (e.g., as caused by the EMR and/or practice management system) receives the PA authentication and/or authorization response 1420.

The provider computing entity (e.g., as caused by the EMR and/or practice management system operating thereon) may then provide (e.g., transmit) a service order 1422. In an example embodiment, the service order 1422 is encrypted using, for example, the authentication token. For example, the mediator module 222 may receive the service order 1422. In various embodiments, the service order 1422 comprises the trigger indication, information/data that causes and/or triggers the listener 220 to generate the trigger indication, and/or information/data that may be used to generate a trigger indication. In various embodiments, the mediator module 222 may check the authorization token to ensure that the provider corresponding to the service order 1422 is authorized, authenticated, and/or appropriately credentialed to place the service order (e.g., order the lab work and/or prescribe the prescription. After and/or responsive to the mediator module 222 determining that the provider corresponding to the service order 1422 is authorized, authenticated, and/or appropriately credentialed to order the service (e.g., order the lab work, prescribe the prescription) indicated in the service order 1422, the mediator module 222 may reformat the service order 1422 and/or translate the service order 1422 to generate a service request 1424. For example, the service request 1424 may be and/or comprise a care estimate trigger indication. For example, various EMR and/or practice management systems may generate and provide service orders having a variety of formats. The mediator module 222 may be configured and/or programmed to convert and/or translate the service order 1422 into a standardized service request 1424 format. The mediator module 222 may then provide the service request 1424.

The authorization module 228 may receive the service request 1424. Responsive to receiving and/or reading the service request 1424 (e.g., receiving and/or reading the trigger indication), the authorization module 228 may perform a PA check to determine if the patient/member needs prior authorization for receiving the service(s) indicated in the service request 1424 and, if PA is required, documenting that PA is provided. The authorization module 228 may then generate and forward a care estimate inquiry 1426 comprising the trigger indication and PA information/data to the care estimate module 230.

The care estimate module 230 may perform the care estimate and generate the care estimate notification. In an example embodiment, the care estimate is performed based at least in part on the PA information/data received in the care estimate inquiry 1426. For example, as described above, the care estimate module 230 may identify one or more potential providers within a predefined and/or user-configurable distance threshold for each service indicated in the trigger indication (e.g., included in the care estimate inquiry 1426). The care estimate module 230 may then determine cost estimates for each potential provider for each service. The care estimate module 230 may then generate and provide a care estimate response 1428 comprising the potential providers identified for each service and corresponding provider information/data (e.g., provider name, provider location, provider contact information/data) and corresponding cost estimates for the potential provider to provide the service.

The authorization module 228 may receive the care estimate response 1428 and may provide a lab/pharmacy confirmation request 1430 to the lab module 232 and/or RX module 234. For example, the lab/pharmacy confirmation request 1430 may include PA information/data and/or information/data from the care estimate response 1428. The lab module 232 and/or RX module 234 may provide the PA information/data to one or more potential providers for the service (e.g., to enable scheduling of the service with the potential provider), request that a cost estimate for the service to be performed by the provider be confirmed, and/or the like. The lab module 232 and/or RX module 234 may then generate and provide a service confirmation 1432. The service confirmation 1432 may include a confirmation of receipt of the PA information/data, a confirmation of one or more cost estimates, scheduling availability for one or more potential providers to provide the service, and/or the like.

The authorization module 228 receives the service confirmation 1432 and, based thereon, generates a confirmed care estimate response 1434. For example, the authorization module 228 may update one or more cost estimates of the care estimate response 1428 based on the service confirmation 1432, remove or add one or more potential providers for a service based on the service confirmation 1432, add scheduling information/data to the care estimate response 1428 based on the service confirmation 1432, add PA information/data to the care estimate response 1428, and/or the like to generate the confirmed care estimate response

1434. The authorization module 228 may then provide the confirmed care estimate response 1434.

The mediator module may receive the confirmed care estimate response 1434. Responsive to receiving and/or reading the confirmed care estimate response 1434, the mediator module may convert and/or translate the confirmed care estimate response 1434 into a care estimate notification 1436. For example, in various embodiments, the mediator module 222 may convert and/or translate the confirmed care estimate response 1434 into a format corresponding to the EMR and/or practice management system in communication with and/or being operated by the provider computing entity. For example, the service order 1422 may include an indication of the EMR and/or practice management system in communication with and/or being operated by the provider computing entity and the conversion and/or translation of the service order 1422 to the care estimate inquiry 1424 and/or conversion and/or translation of the confirmed care estimate response 1434 to the care estimate notification 1436 may be based at least in part on the EMR and/or practice management system in communication with and/or operating on the provider computing entity. In an example embodiment, the care estimate notification 1436 may be encrypted. For example, the care estimate notification 1436 may be encrypted such that the authentication token is required for decrypting, reading, and/or extracting information from the care estimate notification 1436.

The provider computing entity and/or a patient/member computing entity may receive, read, and/or analyze the care estimate notification and provide and/or display a care estimate evaluation IUI 900 corresponding to the EMR and/or practice management system operated by and/or on behalf of the provider. For example, a patient/member computing entity corresponding to the patient/member indicated in the service order 1422 may receive the care estimate notification (e.g., via SMS message, MMS message, instant message, email, an online portal, a dedicated application, and/or the like). The patient/member may review the cost estimate evaluation (e.g., via an IUI provided via the patient/member computing entity), select a provider for each service of the cost estimate evaluation, schedule the service with the provider, and/or the like.

V. Conclusion

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method comprising:
receiving, by one or more processors and from a point-of-care (POC) system accessible by a provider, a trigger indication that comprises (a) provider identifying information that identifies, among a plurality of providers, the provider having access to the POC system and (b) patient identifying information that identifies a patient, a location of the patient, and a service;
extracting, by the one or more processors, the patient identifying information from the trigger indication;
determining, by the one or more processors, an Application Programing Interface (API) call for requesting additional patient information from the POC system based at least in part on the provider identifying information within the trigger indication;
transmitting, by the one or more processors, the API call to the POC system to request the additional patient information;
in response to the API call, receiving, by the one or more processors and from the POC system, eligibility information for the patient and the service, wherein the eligibility information for the patient matches at least a portion of the patient identifying information;
determining, by the one or more processors, a potential provider that provides the service based at least in part on the eligibility information, the patient identifying information, the additional patient information, the location of the patient, and a location associated with the potential provider;
transmitting, by the one or more processors, a cost estimate request API call to one or more external computing systems of the potential provider to determine a cost estimate for providing the service to the patient, wherein the cost estimate request API call comprises at least a portion of the eligibility information associated with the patient;
generating, by the one or more processors, a care estimate notification that (a) has a format readable by the POC system based at least in part on the provider identifying information within the trigger indication, (b) identifies the potential provider and (c) comprises the cost estimate;
encrypting, by the one or more processors, the care estimate notification based at least in part on an authentication token; and
transmitting, by the one or more processors and to the POC system, the care estimate notification, causing the POC system to (a) decrypt the care estimate notification utilizing the authentication token and (b) provide a graphical representation of a care estimate evaluation comprising at least a portion of the care estimate notification within a user interface.

2. The method of claim 1, wherein the service is a procedure, lab work, or a prescription.

3. The method of claim 1, further comprising performing an eligibility check using the patient identifying information to determine the eligibility information.

4. The method of claim 1, further comprising performing an authentication of the provider identified in the trigger indication prior to providing the care estimate notification, and wherein encrypting the care estimate notification comprises encrypting the care estimate notification based at least in part on the authentication.

5. The method of claim 1, wherein the care estimate notification comprises scheduling information for scheduling the service with the potential provider.

6. The method of claim 1, wherein the trigger indication is generated in response to a trigger being identified by a listener operating on the one or more processors.

7. An apparatus comprising at least one processor, at least one communications interface, and at least one memory including computer program code, the computer program code comprising executable instructions, the at least one memory and computer program code configured to, with the at least one processor, cause the apparatus to at least:
receive, from a point-of-care (POC) system accessible by a provider, a trigger indication that comprises (a)

provider identifying information that identifies, among a plurality of providers, the provider having access to the POC system and (b) patient identifying information that identifies a patient, a location of the patient, and a service;

extract the patient identifying information from the trigger indication;

determine an Application Programing Interface (API) call for requesting additional patient information from the POC system based at least in part on the provider identifying information within the trigger indication;

transmit the API call to the POC system to request the additional patient information;

in response to the API call, receive eligibility information for the patient and the service from the POC system, wherein the eligibility information for the patient matches at least a portion of the patient identifying information;

determine a potential provider that provides the service based at least in part on the eligibility information, the patient identifying information, the additional patient information, the location of the patient, and a location associated with the potential provider;

transmitting a cost estimate request API call to one or more external computing systems of the potential provider to determine a cost estimate for providing the service to the patient, wherein the cost estimate request API call comprises at least a portion of the eligibility information associated with the patient;

generate a care estimate notification that (a) has a format readable by the POC system based at least in part on the provider identifying information within the trigger indication, (b) identifies the potential provider and (c) comprises the cost estimate;

encrypt the care estimate notification based at least in part on an authentication token; and transmit the care estimate notification to the POC system to cause the POC system to (a) decrypt the care estimate notification utilizing the authentication token and (b) provide a graphical representation of a care estimate evaluation comprising at least a portion of the care estimate notification within a user interface.

8. The apparatus of claim 7, wherein the service is a procedure, lab work, or a prescription.

9. The apparatus of claim 7, wherein the at least one memory and computer program code are further configured to, with the at least one processor, cause the apparatus to at least perform an eligibility check using the patient identifying information to determine the eligibility information.

10. The apparatus of claim 7, wherein the at least one memory and computer program code are further configured to, with the at least one processor, cause the apparatus to at least perform an authentication of the provider identified in the trigger indication prior to providing the care estimate notification, and wherein encrypting the care estimate notification comprises encrypting the care estimate notification based at least in part on the authentication.

11. The apparatus of claim 7, wherein the care estimate notification comprises scheduling information for scheduling the service with the potential provider.

12. The apparatus of claim 7, wherein the trigger indication is generated in response to a trigger being identified by a listener.

13. A computer program product comprising at least one non-transitory computer-readable storage medium having computer-executable program code portions stored therein, the computer-executable program code portions comprising computer program code instructions, the computer program code instructions, when executed by a processor of a computing entity, are configured to cause the computing entity to:

receive, from a point-of-care (POC) system accessible by a provider, a trigger indication that comprises (a) provider identifying information that identifies, among a plurality of providers, the provider having access to the POC system and (b) patient identifying information that identifies a patient, a location of the patient, and a service;

extract the patient identifying information from the trigger indication;

determine an Application Programing Interface (API) call for requesting additional patient information from the POC system based at least in part on the provider identifying information within the trigger indication;

transmit the API call to the POC system to request the additional patient information;

in response to the API call receive eligibility information for the patient and the service from the POC system, wherein the eligibility information for the patient matches at least a portion of the patient identifying information;

determine a potential provider that provides the service based at least in part on the eligibility information, the patient identifying information, the additional patient information, the location of the patient, and a location associated with the potential provider;

transmit a cost estimate request API call to one or more external computing systems of the potential provider to determine a cost estimate for providing the service to the patient, wherein the cost estimate request API call comprises at least a portion of the eligibility information associated with the patient;

generate a care estimate notification that (a) has a format readable by the POC system based at least in part on the provider identifying information within the trigger indication, (b) identifies the potential provider and (c) comprises the cost estimate;

encrypt the care estimate notification based at least in part on an authentication token; and transmit the care estimate notification to the POC system to cause the POC system to (a) decrypt the care estimate notification utilizing the authentication token and (b) provide a graphical representation of a care estimate evaluation comprising at least a portion of the care estimate notification within a user interface.

14. The computer program product of claim 13, wherein the service is a procedure, lab work, or a prescription.

15. The computer program product of claim 13, wherein the computer program code instructions, when executed by the processor of the computing entity, are further configured to cause the computing entity to:

perform an authentication of a provider identified in the trigger indication prior to providing the care estimate notification; and wherein encrypting the care estimate notification comprises encrypting the care estimate notification based at least in part on the authentication of the provider.

16. The computer program product of claim 13, wherein the care estimate notification comprises scheduling information for scheduling the service with the potential provider.

* * * * *